United States Patent
Follstad et al.

(10) Patent No.: US 11,292,829 B2
(45) Date of Patent: Apr. 5, 2022

(54) MAMMALIAN CELL CULTURE

(75) Inventors: Brian D. Follstad, Seattle, WA (US);
Rebecca E. McCoy, Port Orchard, WA (US); Arvia E. Morris, Seattle, WA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/127,050

(22) PCT Filed: Jun. 29, 2012

(86) PCT No.: PCT/US2012/045070
§ 371 (c)(1),
(2), (4) Date: Apr. 10, 2014

(87) PCT Pub. No.: WO2013/006479
PCT Pub. Date: Jan. 10, 2013

(65) Prior Publication Data
US 2014/0255993 A1    Sep. 11, 2014

Related U.S. Application Data

(60) Provisional application No. 61/503,737, filed on Jul. 1, 2011.

(51) Int. Cl.
| | | |
|---|---|---|
| C07K 16/00 | (2006.01) | |
| C12P 21/00 | (2006.01) | |
| C12N 5/00 | (2006.01) | |
| C12P 21/02 | (2006.01) | |

(52) U.S. Cl.
CPC ............ *C07K 16/00* (2013.01); *C12N 5/0037* (2013.01); *C12P 21/00* (2013.01); *C12P 21/02* (2013.01); *C07K 2317/14* (2013.01); *C12N 2500/32* (2013.01); *C12N 2510/02* (2013.01); *C12N 2523/00* (2013.01)

(58) Field of Classification Search
CPC .................................................. C12N 2500/90
See application file for complete search history.

(56) References Cited

U.S. PATENT DOCUMENTS

| | | | |
|---|---|---|---|
| 4,499,064 A | 2/1985 | Shive | |
| 4,816,401 A * | 3/1989 | Taupier ................ | C12N 5/0037 435/406 |
| 5,045,468 A * | 9/1991 | Darfler ................... | C12N 5/163 435/395 |
| 5,324,656 A * | 6/1994 | Ham ..................... | C12N 5/0659 435/384 |
| 5,795,781 A * | 8/1998 | Wille, Jr. ............... | A61L 27/38 435/383 |
| 6,544,424 B1 | 4/2003 | Shevitz | |
| 7,037,721 B1 * | 5/2006 | Wille, Jr. ............. | C12N 5/0629 435/325 |
| 7,598,083 B2 * | 10/2009 | Epstein ................. | C12N 5/005 435/325 |
| 2004/0048368 A1 | 3/2004 | Chen et al. | |
| 2008/0206819 A1 * | 8/2008 | Tsao ...................... | C12N 5/0018 435/70.3 |
| 2011/0086411 A1 | 4/2011 | Grillberger et al. | |
| 2019/0292513 A1 * | 9/2019 | Desai ...................... | C12P 19/04 |

FOREIGN PATENT DOCUMENTS

| | | | |
|---|---|---|---|
| WO | | 93/05145 A | 3/1993 |
| WO | | 95/24484 A1 | 9/1995 |
| WO | | 98/45411 A | 10/1998 |
| WO | | 2002/101019 A | 12/2002 |
| WO | | 03/027248 A | 4/2003 |
| WO | | 2003/083066 A2 | 10/2003 |
| WO | | 2006/026445 A1 | 3/2006 |
| WO | WO | 2006/026445 A1 | 3/2006 |
| WO | | 2006/128908 A1 | 12/2006 |
| WO | | 2008/063892 A2 | 5/2008 |
| WO | | 2008/154014 A2 | 12/2008 |
| WO | | 2009/023562 A2 | 2/2009 |
| WO | | 2011/014838 A1 | 2/2009 |
| WO | | 2011/062926 A2 | 11/2009 |
| WO | WO | 11/019619 A1 | 2/2011 |
| WO | | 2011/065940 A1 | 6/2011 |

OTHER PUBLICATIONS

Seewoster et al. 1995. Influence of targeted asparagine starvation on extra- and intracellular amino acid pools of cultivated Chinese hamster ovary cells. Appl Microbiol Biotechnol. Dec. 1995;44(3-4):344-50.*
Naderi et al. 2011; Metaboloc analysis of a CHO cell line in batch and fed-batch culture. on the web at: uwspace.uwaterloo.ca/bitstream/handle/10012/6333/Naderi_Saeideh.pdf?sequence=1 &isAllowed=y.*
Clinke et al. 2011; Study of a recombinant CHO cell line producing a monoclonal antibody by ATF or TFF external filter perfusion in a SAVE bioreactorTM . BMC Proceedings 5(Suppl 8):P105.*
Leelavatcharamas et al. 1999; Use of a cell cycle analysis to characterise growth and interferon-_ production in perfusion culture of CHO cells. Cytotechnology. 30: 59-69.*
Schroder et al. 2004; Serum- and protein-free media formulations for the Chinese hamster ovary cell line DUKXB11. J. Biotechnology. 108: 279-292.*
Su et al. 1998; Size control: Cell proliferation does not equal growth. Curr. Biol. 8(19): R687-R689.*
Kaldis. 2016; Quo vadis cell growth and division? Fronteries in Cell and Developmental Biology. 4, Article 95, pp. 1-4.*
Zhang et al. 2013; Rational development of serum-free medium and fed-batch process for a GS-CHO cell line expressing recombinant antibody. Cytotechnology. 65: 363-378.*

(Continued)

*Primary Examiner* — Karen Cochrane Carlson

(57) ABSTRACT

The invention provides a method for culturing mammalian cells. The method provides greater control over cell growth to achieve high product titer cell cultures by changing the temperature of the cell culture and/or by starving the cells in their asparagine supply.

41 Claims, 23 Drawing Sheets

(56) References Cited

OTHER PUBLICATIONS

Duarte et al. 2014; Metabolic responses of CHO cells to limitation of key amino acids. Biotechnology and Bioengineering. 111(10:2095-2106.*
Kumar et al., Proliferation Control Strategies to Improve Productivity and Survival During CHO Based Production Culture. Cytotechnology, Mar. 1, 2007, vol. 53, No. 1-3, pp. 33-46.
Fomina-Yadlin et al., Cellular Responses to Individual Amino-Acid Depletion in Antibody-Expressing and Parental CHO Cell Lines. Biotechnol. Bioeng., Dec. 11, 2013, vol. 111, No. 5, pp. 965-979.
Chen Z-L, et al., "Temperature shift as a process optimization step for the production of pro-urokinase by a recombinant Chinese hamster ovary cell line in high-density perfusion culture," J. Bioscience and Bioeng. vol. 97, No. 4, pp. 239-243 (2004).
Jeng-Dar, Yang et al., "Achievement of high cell density and high antibody productivity by a controlled-fed perfusion bioreactor process," Biotech. and Bioeng. vol. 69, No. 1, pp. 74-82 (2000).
Hayter, P.M. et al., "Chinese hamster ovary cell growth and interferon production kinetics in stirred batch culture," Appl. Microbiol. and Biotech., vol. 34, pp. 559-564 (1991).
Chu, L. et al., "Industrial choices for protein production by large-scale cell culture," Current Opinion in Biotech. vol. 12, pp. 180-187 (2001).
Jee Yon Kim et al., "CHO cells in biotechnology for production of recombinant proteins: current state and further potential," Applied Microbiol. and Biotech. vol. 93, No. 3, pp. 917-930 (2011).
Sauer, Paul W. et al., "A high-yielding, generic fed-batch cell culture process for production of recombinant antibodies," Biotech. and BioEng. vol. 67, No. 5, pp. 585-597 (2000).
Butler, Michael, "Animal cell cultures: recent achievements and perspectives in the production of biopharmaceuticals," Applied Microbiol. and Biotech, vol. 68, No. 3, pp. 283-291 (2005).
Rodriguez, J., et al., "High productivity of human recombinant beta-interferon from a low-temperature perfusion culture," J. Biotechnol. vol. 150, No. 4, pp. 509-518 (2010).
Lipscomb, Matthew L., et al. "Production of a secreted glycoprotein from an inducible promoter system in a perfusion bioreactor," Biotech. Progress, American Institute of Chem. Engineers, vol. 20, No. 5, pp. 1402-1407 (2004).
Gramer, et al., Comparison of cell growth in T-Flasks, in micro hollow fiber bioreactors, and in an industrial scale hollow fiber bioreactor system, Cytotechnology, 34:111-119, 2000.
Gloeckner, et al., Monitoring of cell viability and cell growth in a hollow-fiber bioreactor by use of the dye Alamar Blue, JIM, 252:131-138, 2001.
Bioconcept, Cell Catalogue, Culture 2004.
Dissertation of J. E. Dowd: 'Predictive control and optimization of bioprocesses for recombinant t-PA protein production by mammalian cells', 2000.
Dowd et al., "Optimization and control of perfusion cultures using a viable cell probe and cell specific perfusion rates", Cytotechnology 42, pp. 35-45, May 2003.
Excerpt of'VWR', "Determination of biomass in suspension cell cultures with VoluPAC tubes", Issue 16, pp. 12-13, 2006.
Furukawa et al., "Enhancement of productivity of recombinant a-amidating enzyme by low temperature culture" Cytotechnology 31, pp. 85-94, 1999.
Gorenflo et al., "Scale-up and optimization of an acoustic filter for 200 L/day perfusion of a CHO cell culture" Biotechnology and Bioengineering 80(4 ), pp. 438-444, Nov. 20, 2002.
Gorfien et al., "Optimized Nutrient Additives for Fed-Batch Cultures" Bio Pharm International, pp. 34-40, Apr. 2003.
Greco et al., "Organization and expression of the cell cycle gene, ts11, that encodes asparagine synthetase", Molecular and Cellular Biology, 9(6), pp. 2350-2359, Jun. 1989.
Griffiths et al., "Maximisation of perfusion systems and process comparison with batch-type cultures. Maximisation of perfusion cultures", Cytotechnoloy 9, pp. 3-9, 1992.
Hu et al., "Bioprocess development for the production of mouse-human chimeric anti-epidermal growth factor receptor vIII antibody C12 by suspension culture of recombinant Chinese hamster ovary cells" Cytotechnology 63, pp. 247-258, Feb. 5, 2011.
Huang et al., "Process development for a recombinant Chinese hamster ovary (CHO) cell line utilizing a metal induced and amplified metallothionein expression system" Biotechnology and Bioengineering 88(4), pp. 437-450, Sep. 21, 2004.
Khattak et al., "Feed development for fed-batch CHO production process by semisteady state analysis" Biotechnol, Prog, 26(3), pp. 797-804, Dec. 11, 2009.
Khetan et al., "Control of misincorporation of serine for asparagine during antibody production using CHO cells" Biotechnology and Bioengineering, 107(1), pp. 116-123, Apr. 26, 2010.
Kim et al., "Application of a cell-once-through perfusion strategy for production of recombinant antibody from rCHO cells in a Centritech Lab II centrifuge system" Biotechnol. Prog, 23, pp. 1186-1197, Aug. 11, 2007.
Kim et al., "Limited use of Centritech Lab II Centrifuge in perfusion culture of rCHO cells for the production of recombinant antibody", Biotechnol. Prog. 24, pp. 166-174, Dec. 20, 2007.
Lonza 'Cell Discovery Research Products Catalog', 2009-2010.
Meuwly et al., "Optimization of the medium perfusion rate in a packed-bed bioreactor charged with CHO cells" Cytotechnology, 46, pp. 37-47, Sep. 2004.
Ozturk, "Engineering challenges in high density cell culture systems" Cytotechnology 22, pp. 3-16, Jan. 1996.
Patterson and Maxwell, "Effects of L-asparagine deprivation on the cell cycle of the Jensen sarcoma" Cancer Research 30, pp. 1064-1067, Apr. 1970.
Stettler et al., "New disposable tubes for rapid and precise biomass assessment for suspension cultures of mammalian cells" Biotechnology and Bioengineering, 95(6), pp. 1228-1233, Jul. 25, 2006.
Wang, et al., 'Biological Drug Products: Development and Strategies' 2014.
Werner et al., "Serum-free production of a chimeric E-selectin-IgG protein from 1 to 100 1 scale: Repeated batch cultivation versus continuous spin filter perfusion" Cytotechnology 38, pp. 47-56, 2002.
Xing et al., "Optimizing amino acid composition of CHO cell culture media for a fusion protein production", Process Biochemistry 46, pp. 1423-1429, Mar. 29, 2011.
Zhu et al., "Effects of elevated pCO2 and osmolality on growth of CHO cells and production of antibody-fusion protein B1: a case study" Biotechnol, Prog, 21, pp. 70-77, Jan.-Feb. 2005.
Carvalhal, et al., "Cell Growth Arrest by Nucleotides, Nucleosides and Bases as a Tool for Improved Production of Recombinant Proteins" *Biotechnol. Prog.*, 19, 69-83, 2003.
Li, et al., "Cell culture processes for monoclonal antibody production" Mabs, Sep.-Oct. 2010., 2(5), pp. 466-479, Epub Sep. 1, 2010.
Pan, et al.. "Selection of chemically defined media for CHO cell fed-batch culture processes" Cytotechnology (2017) 69:39-56.
Whitford, et al., "Interest in Hollow-Fiber Perfusion Bioreactors is Growing" BioProcess International, 7(9), pp. 54-63, Oct. 2009.
Hansen and Emborg, "Extra- and intracellular amino acid concentrations in continuous Chinese hamster ovary cell culture" Appl Microbial Biotechnol, 1994.
Lloyd et al., "The role of the cell cycle in determining gene expression and productivity in CHO cells" Cytotechnology, 1999.
Stanners et al., "Effect of extreme amino acid starvation on the protein synthetic machinery of CHO cells" J Cell Physiol, 1978.
Sunley and Butler, "Strategies for the enhancement of recombinant protein production from mammalian cells by growth arrest" Biotechnology Advances, 2010.
Torpier et al., "Synchronisation de cellules BHK 21 par carence partielle en L-Asparagine" Experimental Cell Research, 1974 (abstract in English).

* cited by examiner

MAMMALIAN CELL CULTURE

CROSS REFERENCE TO RELATED APPLICATIONS

This application is a national stage application under 35 U.S.C. § 371 of International Application No. PCT/US2012/045070, having an international filing date of Jun. 29, 2012; which claims priority to U.S. Provisional Patent Application No. 61/503,737, filed Jul. 1, 2011, which is incorporated herein by reference.

FIELD OF INVENTION

The invention provides a method for culturing mammalian cells. The method provides greater control over cell growth to achieve high product titer cell cultures.

BACKGROUND OF INVENTION

As the demand for greater and greater quantities of therapeutic recombinant proteins increases, positive increases in cell growth, viability and protein production are sought by implementing new methods to improve cell development, media optimization and process control parameters. Much effort is now being placed on process optimization, particularly methods and strategies for growing, feeding, and maintaining production cell cultures.

New cell culture methods that provide even incremental improvements in recombinant protein production are valuable, given the expense of large scale cell culture processes and the growing demand for greater quantities of and lower costs for biological products.

Improvements to cell culture processes, recombinant polypeptide expression, titer, and cell viability that can lead to higher production levels, thereby reducing the costs associated with manufacturing protein therapeutics are needed. The invention fulfills these needs by providing a simple, easy and inexpensive method of controlling cell growth while increasing protein production.

SUMMARY OF THE INVENTION

The present invention provides a method of arresting cell growth in a mammalian cell culture expressing a recombinant protein comprising establishing a mammalian cell culture in a serum-free culture medium in a bioreactor; inducing cell growth-arrest by perfusion with a serum-free perfusion medium having an L-asparagine concentration of 5 mM or less; maintaining the mammalian cells in a growth-arrested state by perfusion with a serum-free perfusion medium having an L-asparagine concentration of 5 mM or less.

The present invention also provides a method of increasing recombinant protein production in a mammalian cell culture expressing a recombinant protein comprising establishing a mammalian cell culture in a serum-free culture medium in a bioreactor; inducing cell growth-arrest by perfusion with a serum-free perfusion medium having an L-asparagine concentration of 5 mM or less; maintaining the mammalian cells in a growth-arrested state by perfusion with a serum-free perfusion medium having an L-asparagine concentration of 5 mM or less. In a related embodiment recombinant protein production in the mammalian cell culture is increased compared to a culture where the cells are not subjected to L-asparagine-induced cell growth-arrest.

The present invention also provides a method of limiting a mammalian cell culture expressing a recombinant protein at a desired packed cell volume comprising establishing a mammalian cell culture in a serum-free culture medium in a bioreactor; inducing cell growth-arrest by perfusion with a serum-free perfusion medium having an L-asparagine concentration of 5 mM or less; maintaining the mammalian cells in a growth-arrested state by perfusion with a serum-free perfusion medium having an L-asparagine concentration of 5 mM or less.

In one embodiment of the present invention, in any of the methods above the perfusion with a serum-free perfusion medium having an L-asparagine concentration of 5 mM or less begins on or before day 3 of the culture. In another embodiment, in any of the methods above induction of cell growth-arrest takes place prior to a production phase. In another embodiment, in any of the methods above induction of cell growth-arrest takes place during a production phase. In another embodiment, in any of the methods above cell growth-arrest is induced by L-asparagine starvation. In yet another embodiment, any of the methods above further comprise a temperature shift from 36° C. to 31° C. In another embodiment, any of the methods above further comprise a temperature shift from 36° C. to 33° C. In a related embodiment the temperature shift occurs at the transition between a growth phase and a production phase. In yet another embodiment the temperature shift occurs during a production phase. In another embodiment the methods above further comprise a packed cell volume during a production phase less than or equal to 35%. In a related embodiment the packed cell volume during a production phase is less than or equal to 35%

The present invention also provides a method of culturing mammalian cells expressing a recombinant protein comprising; establishing a mammalian cell culture in a serum-free culture medium in a bioreactor; growing the mammalian cells during a growth phase and supplementing the culture medium with bolus feeds of a serum-free feed medium, and maintaining the mammalian cells during a production phase by perfusion with a serum-free perfusion medium, wherein the packed cell volume during the production phase is less than or equal to 35%. In one embodiment of the present invention, perfusion begins on or about day 5 to on or about day 9 of the cell culture. In a related embodiment perfusion begins on or about day 5 to on or about day 7 of the cell culture. In one embodiment perfusion begins when the cells have reached a production phase. In another embodiment the method further comprises inducing cell growth-arrest by L-asparagine starvation followed by perfusion with a serum-free perfusion medium having an L-asparagine concentration of 5 mM or less. In yet another embodiment the method further comprises inducing cell growth-arrest by perfusion with a serum-free perfusion medium having an L-asparagine concentration of 5 mM or less.

In one embodiment of the invention the concentration of L-asparagine in the serum-free perfusion medium is less than or equal to 5 mM. In another embodiment the concentration of L-asparagine in the serum-free perfusion medium is less than or equal to 4.0 mM. In another embodiment the concentration of L-asparagine in the serum-free perfusion medium is less than or equal to 3.0 mM. In still another embodiment the concentration of L-asparagine in the serum-free perfusion medium is less than or equal to 2.0 mM. In yet another embodiment the concentration of L-asparagine in the serum-free perfusion medium is less than or equal to 1.0 mM. In yet another embodiment the concentration of L-asparagine in the serum-free perfusion medium is 0 mM. In another embodiment perfusion is performed at a rate that increases during the production phase from 0.25 working volume per day to 1.0 working volume per day during the cell culture. In a related embodiment perfusion is performed at a rate that reaches 1.0 working volume per day on day 9 to day 11 of the cell culture. In another related embodiment perfusion is performed at a rate that reaches 1.0 working volume per day on day 10 of the cell culture. In yet another embodiment the bolus feeds of serum-free feed medium begin on day 3 or day 4 of the cell culture. In another embodiment of the invention the method further comprises a temperature shift from 36° C. to 31° C. In another embodiment the method further comprises a temperature shift from 36° C. to 33° C. In a related embodiment the temperature shift occurs at the transition between the growth phase and production phase. In a related embodiment the temperature shift occurs during the production phase.

In one embodiment of the invention the L-asparagine concentration of the cell culture medium is monitored prior to and during L-asparagine starvation.

In one embodiment of the invention the packed cell volume is less than or equal to 35%. In a related embodiment the packed cell volume is less than or equal to 30%.

In one embodiment of the invention the viable cell density of the mammalian cell culture at a packed cell volume less than or equal to 35% is $10 \times 10^6$ viable cells/ml to $80 \times 10^6$ viable cells/ml. In a related embodiment the viable cell density of the mammalian cell culture is $20 \times 10^6$ viable cells/ml to $30 \times 10^6$ viable cells/ml.

In one embodiment of the invention perfusion comprises continuous perfusion.

In one embodiment of the invention the rate of perfusion is constant.

In one embodiment of the invention perfusion is performed at a rate of less than or equal to 1.0 working volumes per day.

In another embodiment of the invention the mammalian cell culture is established by inoculating the bioreactor with at least $0.5 \times 10^6$ to $3.0 \times 10^6$ cells/mL in a serum-free culture medium. In a related embodiment the mammalian cell culture is established by inoculating the bioreactor with at least $0.5 \times 10^6$ to $1.5 \times 10^6$ cells/mL in a serum-free culture medium.

In another embodiment of the invention the perfusion is accomplished by alternating tangential flow.

In another embodiment of the invention the bioreactor has a capacity of at least 500 L. In a related embodiment the bioreactor has a capacity of at least 500 L to 2000 L. In yet another related embodiment the bioreactor has a capacity of at least 1000 L to 2000 L.

In another embodiment of the invention the mammalian cells are Chinese Hamster Ovary (CHO) cells.

In another embodiment of the invention the recombinant protein is selected from the group consisting of a human antibody, a humanized antibody, a chimeric antibody, a recombinant fusion protein, or a cytokine.

In another embodiment of the invention any of the methods above further comprise a step of harvesting the recombinant protein produced by the cell culture.

In another embodiment of the invention the recombinant protein produced by the cell culture is purified and formulated in a pharmaceutically acceptable formulation.

BRIEF DESCRIPTION OF THE FIGURES

FIG. 1 Fed-batch start: solid square (■) and solid circle (●) Batch start: open square (□) and open circle (○).

FIG. 5 Cultures grown in medium containing 17.3 mM or 5 mM L-asparagine and 4.6 mM or 10 mM L-glutamine. 17.3 mM L-asparagine and 4.6 mM L-glutamine solid diamond (◆) or mM L-asparagine, 10 mM L-glutamine open diamond (◇).

FIG. 6. Cultures at 2 L bench scale and 500 L pilot scale, with 5 mM L-asparagine, 10 mM L-glutamine. Medium containing 5 mM L-asparagine, 10 mM L-glutamine at 2 L bench scale is represented by the solid diamond (◆) and the 500 L pilot scale is represented by the open diamond (◇)

DETAILED DESCRIPTION OF THE INVENTION

Figure 1A:
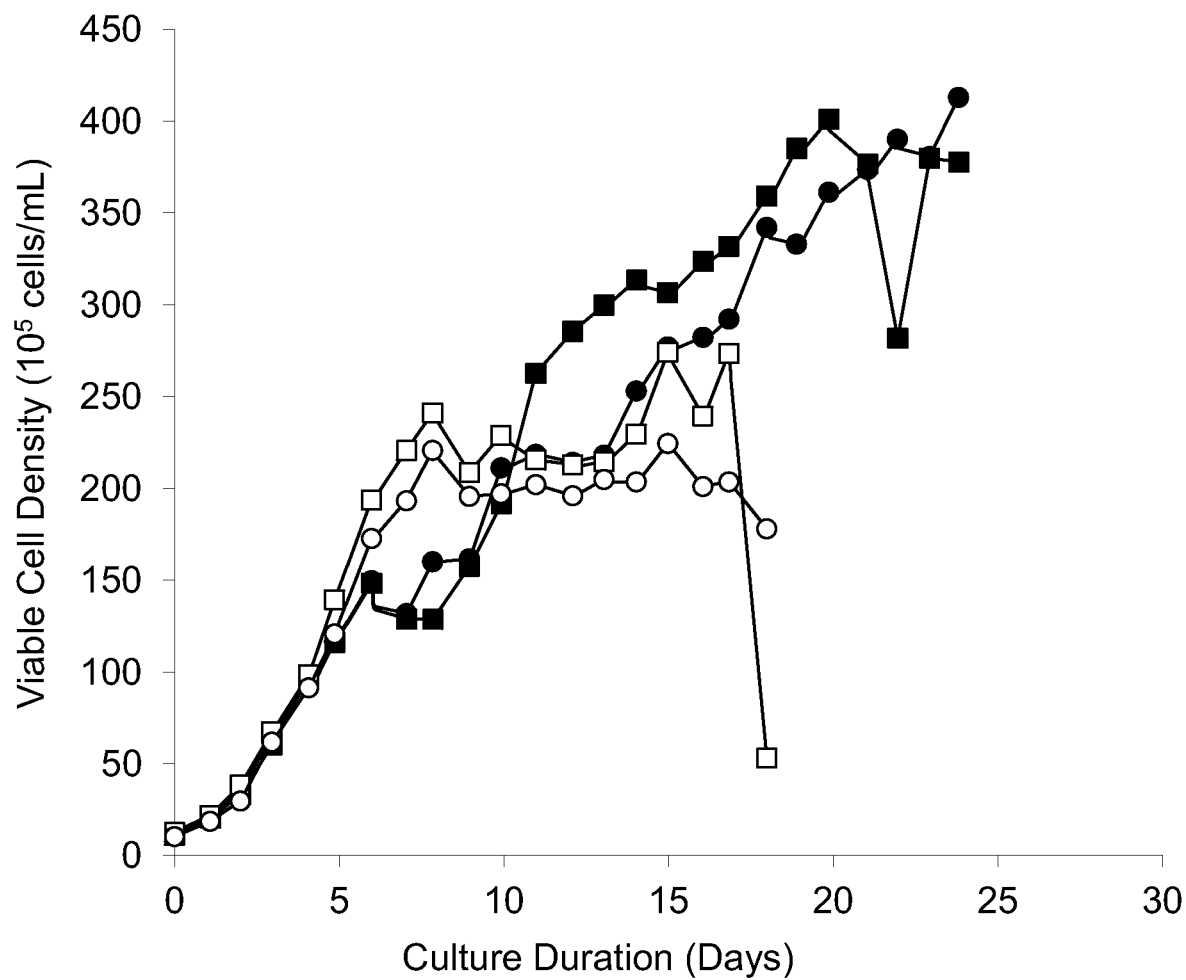
FIG. 1A: Viable cell density.

During recombinant protein production it is desirable to have a controlled system where cells are grown to a desired density and then the physiological state of the cells is switched to a growth-arrested, high productivity state where the cells use energy and substrates to produce the recombinant protein of interest instead of making more cells. Methods for accomplishing this goal, such as temperature shifts and small molecule inducers, are not always successful and can have undesirable effects on product quality. As described herein, packed cell volume can be limited to a desired level during the production phase by inducing cell growth-arrest in the cultured cells by exposure to low L-asparagine conditions. Cell growth-arrest can be achieved and maintained by using a perfusion culture medium that contains a limiting concentration of L-asparagine and maintaining a low concentration of L-asparagine in the cell culture (5 mM or less).

It was also found that the growth-arrested cells showed increased productivity when growth-arrest was initiated by low L-asparagine or through L-asparagine starvation and the growth-arrested cells were subsequently maintained with the cell culture and perfusion medium having an L-asparagine concentration of 5 mM or less.

A growth-arrested, high productivity production phase can be achieved by manipulating the concentration of L-asparagine. As described herein, depletion of L-asparagine resulted in growth-arrest. In a fed-batch culture, once the cell density was sufficiently high (for example ≥20×10$^6$ viable cells/mL), the culture was repeatedly starved of L-asparagine despite repeated feedings due to consumption of L-asparagine and/or the conversion to L-aspartate. In a cell culture, the extracellular L-asparagine can be converted to L-aspartate and ammonia. L-asparagine depletion resulted in cell cycle arrest. During fed-batch, periods when L-asparagine is present in the culture result in increased productivity and periods when L-asparagine has been depleted result in decreased productivity. In the perfused system, L-asparagine is constantly supplied, total depletion is therefor avoided, and higher concentrations of L-asparagine can be sustained, thus allowing cells to continue multiplying and not be exposed to and environment with depleted or limited L-asparagine. Controlling the concentration of L-asparagine at a sufficiently low concentration (such as concentrations 5 mM or less) can keep the cells in a high productivity state while maintaining viability and limiting growth. In a system having bolus and perfusion feeding, the feed medium can be switched from a formulation containing a high (growth promoting) level of L-asparagine during bolus feeds to a lower (growth-arresting) level of L-asparagine during perfusion feeding. Cell cultures that have been growth-arrested by limiting L-asparagine can be stimulated into a high productivity state by adding back low levels of L-asparagine.

For commercial scale cell culture and the manufacture of biological therapeutics, the ability to arrest cell growth and being able to maintain the cells in a growth-arrested state during the production phase would be very desirable. Having cells that were also induced to increase productivity while in the growth-arrested state and being able to maintain this increased productivity, is ideal for manufacturing purposes.

Provided herein is a method of arresting cell growth in a mammalian cell culture expressing a recombinant protein. The method includes inducing cell growth-arrest in a mammalian cell culture by subjecting the cell culture to serum-free medium having an L-asparagine concentration of 5 mM or less which includes 0 mM L-asparageine). Such induction can be initiated by L-asparagine starvation or by creating a low L-asparagine environment by perfusing the culture with a serum-free perfusion medium having an L-asparagine concentration of 5 mM or less and maintaining the culture in a low L-asparagine environment. The cell culture is then maintained in the growth-arrested state by perfusing with a serum-free perfusion medium with an L-asparagine at a concentration of 5 mM or less and maintaining the culture in the low L-asparagine environment.

Also provided is a method for increasing recombinant protein production in a mammalian cell culture expressing a recombinant protein by inducing a low asparagine cell growth-arrest in a mammalian cell culture. Mammalian cells maintained in the low asparagine growth-arrested state exhibited greater productivity (g protein/cell/day and g protein/cell mass/day) than those which were not low asparagine growth-arrested.

Such method is also useful for limiting a mammalian cell culture at a desired packed cell volume. Packed cell volume during the production phase could be limited at a desired level by reducing L-asparagine levels in the production culture medium. Asparagine concentrations of 5 mM or less in the perfusion medium were sufficient to control cell growth during culture and limit to a desired packed cell volume.

The methods described herein provide greater control over cell growth to high product titer cell cultures; and as such can simplify the gassing strategy compared to a high biomass perfusion processes and minimize product loss during harvest and downstream processing.

The method begins with establishing a mammalian cell culture in a production bioreactor. Preferably smaller production bioreactors are used, in one embodiment the bioreactors are 500 L to 2000 L. In a preferred embodiment, 1000 L-2000 L bioreactors are used. The seed cell density used to inoculate the bioreactor can have a positive impact on the level of recombinant protein produced. In one embodiment the bioreactor is inoculated with at least 0.5×10$^6$ up to and beyond 3.0×10$^6$ viable cells/mL in a serum-free culture medium. In a preferred embodiment the inoculation is 1.0×10$^6$ viable cells/mL.

The mammalian cells then undergo an exponential growth phase. The cell culture can be maintained without supplemental feeding until a desired cell density is achieved. In one embodiment the cell culture is maintained for up to 3 days without supplemental feeding followed by perfusion with a serum-free perfusion medium having an L-asparagine concentration of 5 mM or less to induce and maintain low L-asparagine growth-arrest. In another embodiment the culture can be inoculated at a desired cell density to begin the production phase without a brief growth phase with cell growth-arrest initiated immediately upon inoculation by perfusing the cell culture with serum-free perfusion medium containing 5 mM or less L-asparagine to induce and maintain low L-asparagine growth-arrest. In any of the embodiments herein the switch from the growth phase to production phase can also be initiated by L-asparagine starvation (subjecting cells to a 0 mM L-asparagine environment) followed by perfusion with a cell culture medium having an L-asparagine concentration of equal to or less than 5 mM. and maintaining the concentrating of L-asparagine in the cell culture at that level.

Without regard as to how low L-asparagine growth-arrest is induced, higher productivity is seen in the growth-arrested cells that are maintained by perfusing with a low L-asparagine medium and maintaining the cell culture at an L-asparagine level of 5 mM or less.

As used herein, "growth-arrest", which may also be referred to as "cell growth-arrest", is the point where cells stop increasing in number or when the cell cycle no longer progresses. Growth-arrest can be monitored by determining the viable cell density of a cell culture. Some cells in a growth-arrested state may increase in size but not number, so the packed cell volume of a growth-arrested culture may increase. Growth-arrest can be reversed to some extent, if the cells are not in declining health, by adding additional L-asparagine to the cell culture.

Growth-arrest is initiated by L-asparagine when the cell density of the culture reaches a level where the concentration of L-asparagine in the culture becomes limiting for continued growth or when the culture is starved of L-asparagine. L-asparagine starvation occurs when the L-asparagine concentration in a cell culture medium is effectively at 0 mM. Starvation can result in growth-arrest within 24 hours. Starvation for longer than 48 hours could damage the health of the cells. To maintain cells in the growth-arrested state, the L-asparagine concentration in the cell culture must be maintained at 5 mM or less. The cell culture medium concentration of L-asparagine required to arrest cell growth is dependent on the ability of the cells to make their own asparagine. For cultures where cells can make their own asparagine, a lower concentration, or even removal of L-asparagine from the medium may be required for growth-arrest. For cultures that are unable to make their own asparagine, for example, cells that lack active asparagine synthetase enzyme, concentrations above zero up to 5 mM L-asparagine could be used to arrest growth.

As used herein, "packed cell volume" (PCV), also referred to as "percent packed cell volume" (% PCV), is the ratio of the volume occupied by the cells, to the total volume of cell culture, expressed as a percentage (see Stettler, wt al., (2006) Biotechnol Bioeng. December 20:95(6):1228-33). Packed cell volume is a function of cell density and cell diameter; increases in packed cell volume could arise from increases in either cell density or cell diameter or both. Packed cell volume is a measure of the solid content in the cell culture. Solids are removed during harvest and downstream purification. More solids mean more effort to separate the solid material from the desired product during harvest and downstream purification steps. Also, the desired product can become trapped in the solids and lost during the harvest process, resulting in a decreased product yield. Since host cells vary in size and cell cultures also contain dead and dying cells and other cellular debris, packed cell volume is a more accurate way to describe the solid content within a cell culture than cell density or viable cell density. For example, a 2000 L culture having a cell density of $50 \times 10^6$ cells/ml would have vastly different packed cell volumes depending on the size of the cells. In addition, some cells, when in a growth-arrested state, will increase in size, so the packed cell volume prior to growth-arrest and post growth-arrest will likely be different, due to increase in biomass as a result to cell size increase.

At the transition between the growth phase and the production phase, and during the production phase, the percent packed cell volume (% PCV) is equal to or less than 35%. The desired packed cell volume maintained during the production phase is equal to or less than 35%. In a preferred embodiment the packed cell volume is equal to or less than 30%. In another preferred embodiment the packed cell volume is equal to or less than 20%. In another preferred embodiment the packed cell volume is equal to or less than 15%. In yet another preferred embodiment the packed cell volume is equal to or less than 10%.

As used herein, "cell density" refers to the number of cells in a given volume of culture medium. "Viable cell density" refers to the number of live cells in a given volume of culture medium, as determined by standard viability assays (such as trypan blue dye exclusion method).

The desired viable cell density at the transition between the growth and production phases and maintained during the production phase is one that provides a packed cell volume of equal to or less than 35%. In one embodiment, the viable cell density is at least about $10 \times 10^6$ viable cells/mL to $80 \times 10^6$ viable cells/mL. In one embodiment the viable cell density is at least about $10 \times 10^6$ viable cells/mL to $70 \times 10^6$ viable cells/mL. In one embodiment the viable cell density is at least about $10 \times 10^6$ viable cells/mL to $60 \times 10^6$ viable cells/mL. In one embodiment the viable cell density is at least about $10 \times 10^6$ viable cells/mL to $50 \times 10^6$ viable cells/mL. In one embodiment the viable cell density is at least about $10 \times 10^6$ viable cells/mL to $40 \times 10^6$ viable cells/mL. In a preferred embodiment the viable cell density is at least about $10 \times 10^6$ viable cells/mL to $30 \times 10^6$ viable cells/mL. In another preferred embodiment the viable cell density is at least about $10 \times 10^6$ viable cells/mL to $20 \times 10^6$ viable cells/mL. In another preferred embodiment, the viable cell density is at least about $20 \times 10^6$ viable cells/mL to $30 \times 10^6$ viable cells/mL. In another preferred embodiment the viable cell density is at least about $20 \times 10^6$ viable cells/mL to at least about $25 \times 10^6$ viable cells/mL, more preferably at least about $20 \times 10^6$ viable cells/mL.

Lower packed cell volume during the production phase helps mitigate dissolved oxygen sparging problems that can hinder higher cell density perfusion cultures. The lower packed cell volume also allows for a smaller media volume which allows for the use of smaller media storage vessels and can be combined with slower flow rates. Lower packed cell volume also has less impact on harvest and downstream processing, compared to higher cell biomass cultures. All of which reduces the costs associated with manufacturing recombinant protein therapeutics.

Three methods are typically used in commercial processes for the production of recombinant proteins by mammalian cell culture: batch culture, fed-batch culture, and perfusion culture. Batch culture, a discontinuous method where cells are grown in a fixed volume of culture media for a short period of time followed by a full harvest. Cultures grown using the batch method experience an increase in cell density until a maximum cell density is reached, followed by a decline in viable cell density as the media components are consumed and levels of metabolic by-products (such as lactate and ammonia) accumulate. Harvest typically occurs at the point when the maximum cell density is achieved (typically $5$-$10 \times 10^6$ cells/mL, depending on media formulation, cell line, etc). The batch process is the simplest culture method, however viable cell density is limited by the nutrient availability and once the cells are at maximum density, the culture declines and production decreases. There is no ability to extend a production phase because the accumulation of waste products and nutrient depletion rapidly lead to culture decline, (typically around 3 to 7 days).

Fed-batch culture improves on the batch process by providing bolus or continuous media feeds to replenish those media components that have been consumed. Since fed-batch cultures receive additional nutrients throughout the run, they have the potential to achieve higher cell densities (>10 to $30 \times 10^6$ cells/ml, depending on media formulation, cell line, etc)) and increased product titers, when compared to the batch method. Unlike the batch process, a biphasic culture can be created and sustained by manipulating feeding strategies and media formulations to distinguish the period of cell proliferation to achieve a desired cell density (the growth phase) from the period of suspended or slow cell growth (the production phase). As such, fed batch cultures have the potential to achieve higher product titers compared to batch cultures. Typically a batch method is used during the growth phase and a fed-batch method used during the production phase, but a fed-batch feeding strategy can be used throughout the entire process. However, unlike the batch process, bioreactor volume is a limiting factor which limits the amount of feed. Also, as with the batch method, metabolic by-product accumulation will lead to culture decline, which limits the duration of the production phase, about 1.5 to 3 weeks. Fed-batch cultures are discontinuous and harvest typically occurs when metabolic by-product levels or culture viability reach predetermined levels.

Perfusion methods offer potential improvement over the batch and fed-batch methods by adding fresh media and simultaneously removing spent media. Typical large scale commercial cell culture strategies strive to reach high cell densities, $60$-$90(+) \times 10^6$ cells/mL where almost a third to over one-half of the reactor volume is biomass. With perfusion culture, extreme cell densities of $>1 \times 10^8$ cells/mL have been achieved and even higher densities are predicted. Typical perfusion cultures begin with a batch culture start-up lasting for a day or two followed by continuous, step-wise and/or intermittent addition of fresh feed media to the culture and simultaneous removal of spend media with the retention of cells and additional high molecular weight compounds such as proteins (based on the filter molecular weight cutoff) throughout the growth and production phases of the culture. Various methods, such as sedimentation, centrifugation, or filtration, can be used to remove spent media, while maintaining cell density. Perfusion flow rates of a fraction of a working volume per day up to many multiple working volumes per day have been reported. An advantage of the perfusion process is that the production culture can be maintained for longer periods than batch or fed-batch culture methods. However, increased media preparation, use, storage and disposal are necessary to support a long term perfusion culture, particularly those with high cell densities, which also need even more nutrients, and all of this drives the production costs even higher, compared to batch and fed batch methods. In addition, higher cell densities can cause problems during production, such as maintaining dissolved oxygen levels and problems with increased gassing including supplying more oxygen and removing more carbon dioxide, which would result in more foaming and the need for alterations to antifoam strategies; as well as during harvest and downstream processing where the efforts required to remove the excessive cell material can result in loss of product, negating the benefit of increased titer due to increased cell mass.

Also provided is a large scale cell culture strategy that combines fed batch feeding during the growth phase followed by continuous perfusion during the production phase. The method targets a production phase where the cell culture is maintained at a packed cell volume of less than or equal to 35%. The method also provides the initiation and maintenance of cell growth-arrest due to low asparagine.

Fed batch culture is a widely-practiced culture method for large scale production of proteins from mammalian cells. See e.g. Chu and Robinson (2001), Current Opin. Biotechnol. 12: 180-87. A fed batch culture of mammalian cells is one in which the culture is fed, either continuously or periodically, with a concentrated feed medium containing nutrients. Feeding can occur on a predetermined schedule of, for example, every day, once every two days, once every three days, etc. When compared to a batch culture, in which no feeding occurs, a fed batch culture can produce greater amounts of recombinant protein. See e.g. U.S. Pat. No. 5,672,502.

In one embodiment, a fed-batch culture with bolus feeds is used to maintain a cell culture during the growth phase. Perfusion feeding can then be used during a production phase. In one embodiment, perfusion begins when the cells have reached a production phase. In another embodiment, perfusion begins on or about day 5 to on or about day 9 of the cell culture. In another embodiment perfusion begins on or about day 5 to on or about day 7 of the cell culture.

In another embodiment the initiation of cell growth-arrest in the fed-batch culture can be initiated by subjecting the fed-batch culture to a period of L-asparagine starvation followed by perfusion with a serum-free perfusion medium having an L-asparagine concentration of 5 mM or less. In one embodiment the L-asparagine concentration of the cell culture medium is monitored prior to and during L-asparagine starvation. In another embodiment the initiation of cell growth-arrest in the fed-batch culture can be achieved by perfusion with a serum free perfusion medium having an L-asparagine concentration of 5 mM or less.

Using bolus feeding during the growth phase allows the cells to transition into the production phase, resulting in less dependence on a temperature shift as a means of initiating and controlling the production phase, however a temperature shift of 36° C. to 31° C. can take place between the growth phase and production phase. In a preferred embodiment the shift is from 36° C. to 33° C.

As described herein, the bioreactor can be inoculated with at least $0.5 \times 10^6$ up to and beyond $3.0 \times 10^6$ viable cells/mL in a serum-free culture medium, preferably 1.0×106 viable cells/mL.

Perfusion culture is one in which the cell culture receives fresh perfusion feed medium while simultaneously removing spent medium. Perfusion can be continuous, step-wise, intermittent, or a combination of any or all of any of these. Perfusion rates can be less than a working volume to many working volumes per day. Preferably the cells are retained in the culture and the spent medium that is removed is substantially free of cells or has significantly fewer cells than the culture. Recombinant proteins expressed by the cell culture can also be retained in the culture. Perfusion can be accomplished by a number of means including centrifugation, sedimentation, or filtration, See e.g. Voisard et al., (2003), Biotechnology and Bioengineering 82:751-65. A preferred filtration method is alternating tangential flow filtration. Alternating tangential flow is maintained by pumping medium through hollow-fiber filter modules. See e.g. U.S. Pat. No. 6,544,424; Furey (2002) Gen. Eng. News. 22 (7), 62-63.

As used herein, "perfusion flow rate" is the amount of media that is passed through (added and removed) from a bioreactor, typically expressed as some portion or multiple of the working volume, in a given time. "Working volume" refers to the amount of bioreactor volume used for cell culture. In one embodiment the perfusion flow rate is one working volume or less per day. Perfusion feed medium can be formulated to maximize perfusion nutrient concentration to minimize perfusion rate.

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate. Fluidized bed bioreactors, hollow fiber bioreactors, roller bottles, shake flasks, or stirred tank bioreactors, with or without microcarriers, can be used. In one embodiment 500 L to 2000 L bioreactors are used. In a preferred embodiment, 1000 L to 2000 L bioreactors are used.

For the purposes of this invention, cell culture medium is a media suitable for growth of animal cells, such as mammalian cells, in in vitro cell culture. Cell culture media formulations are well known in the art. Typically, cell culture media are comprised of buffers, salts, carbohydrates, amino acids, vitamins and trace essential elements. "Serum-free" applies to a cell culture medium that does not contain animal sera, such as fetal bovine serum. Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kans.), among others.

Serum-free versions of such culture media are also available. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

Cell cultures can be supplemented with concentrated feed medium containing components, such as nutrients and amino acids, which are consumed during the course of the production phase of the cell culture. Concentrated feed medium may be based on just about any cell culture media formulation. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal amount. Concentrated feed media are often used in fed batch culture processes.

The method according to the present invention may be used to improve the production of recombinant proteins in multiple phase culture processes. In a multiple stage process, cells are cultured in two or more distinct phases. For example cells may be cultured first in one or more growth phases, under environmental conditions that maximize cell proliferation and viability, then transferred to a production phase, under conditions that maximize protein production. In a commercial process for production of a protein by mammalian cells, there are commonly multiple, for example, at least about 2, 3, 4, 5, 6, 7, 8, 9, or 10 growth phases that occur in different culture vessels preceding a final production culture. The growth and production phases may be preceded by, or separated by, one or more transition phases. In multiple phase processes, the method according to the present invention can be employed at least during the growth and production phase of the final production phase of a commercial cell culture, although it may also be employed in a preceding growth phase. A production phase can be conducted at large scale. A large scale process can be conducted in a volume of at least about 100, 500, 1000, 2000, 3000, 5000, 7000, 8000, 10,000, 15,000, 20,000 liters. In a preferred embodiment production is conducted in 500 L, 1000 L and/or 2000 L bioreactors. A growth phase may occur at a higher temperature than a production phase. For example, a growth phase may occur at a first temperature from about 35° C. to about 38° C., and a production phase may occur at a second temperature from about 29° C. to about 37° C., optionally from about 30° C. to about 36° C. or from about 30° C. to about 34° C. In addition, chemical inducers of protein production, such as, for example, caffeine, butyrate, and hexamethylene bisacetamide (HMBA), may be added at the same time as, before, and/or after a temperature shift. If inducers are added after a temperature shift, they can be added from one hour to five days after the temperature shift, optionally from one to two days after the temperature shift. The cell cultures can be maintained for days or even weeks while the cells produce the desired protein(s).

Samples from the cell culture can be monitored and evaluated using any of the analytical techniques known in the art. Variety of parameters including recombinant protein and medium quality and characteristics can be monitored for the duration of the culture. Samples can be taken and monitored intermittently at a desirable frequency, including continuous monitoring, real time or near real time. In one embodiment the L-asparagine concentration of the cell culture medium is monitored prior to and during L-asparagine starvation.

Typically the cell cultures that precede the final production culture (N−x to N−1) are used to generate the seed cells that will be used to inoculate the production bioreactor, the N−1 culture. The seed cell density can have a positive impact on the level of recombinant protein produced. Product levels tend to increase with increasing seed density. Improvement in titer is tied not only to higher seed density, but is likely to be influenced by the metabolic and cell cycle state of the cells that are placed into production.

Seed cells can be produced by any culture method. A preferred method is a perfusion culture using alternating tangential flow filtration. An N−1 bioreactor can be run using alternating tangential flow filtration to provide cells at high density to inoculate a production bioreactor. The N−1 stage may be used to grow cells to densities of >90×10$^6$ cells/mL. The N−1 bioreactor can be used to generate bolus seed cultures or can be used as a rolling seed stock culture that could be maintained to seed multiple production bioreactors at high seed cell density. The duration of the growth stage of production can range from 7 to 14 days and can be designed so as to maintain cells in exponential growth prior to inoculation of the production bioreactor. Perfusion rates, medium formulation and timing are optimized to grow cells and deliver them to the production bioreactor in a state that is most conducive to optimizing their production. Seed cell densities of >15×10$^6$ cells/mL can be achieved for seeding production bioreactors. Higher seed cell densities at inoculation can decrease or even eliminate the time needed to reach a desired production density.

The invention finds particular utility in improving cell growth, viability and/or protein production via cell culture processes. The cell lines (also referred to as "host cells") used in the invention are genetically engineered to express a polypeptide of commercial or scientific interest. Cell lines are typically derived from a lineage arising from a primary culture that can be maintained in culture for an unlimited time. Genetically engineering the cell line involves transfecting, transforming or transducing the cells with a recombinant polynucleotide molecule, and/or otherwise altering (e.g., by homologous recombination and gene activation or fusion of a recombinant cell with a non-recombinant cell) so as to cause the host cell to express a desired recombinant polypeptide. Methods and vectors for genetically engineering cells and/or cell lines to express a polypeptide of interest are well known to those of skill in the art; for example, various techniques are illustrated in *Current Protocols in Molecular Biology*, Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., *Large Scale Mammalian Cell Culture,* 1990, pp. 15-69.

Animal cell lines are derived from cells whose progenitors were derived from a multi-cellular animal. One type of animal cell line is a mammalian cell line. A wide variety of mammalian cell lines suitable for growth in culture are available from the American Type Culture Collection (Manassas, Va.) and commercial vendors. Examples of cell lines commonly used in the industry include VERO, BHK, HeLa, CV1 (including Cos), MDCK, 293, 3T3, myeloma cell lines (e.g., NSO, NS1), PC12, WI38 cells, and Chinese hamster ovary (CHO) cells. CHO cells are widely used for the production of complex recombinant proteins, e.g. cytokines, clotting factors, and antibodies (Brasel et al. (1996), *Blood* 88:2004-2012; Kaufman et al. (1988), *J. Biol Chem* 263: 6352-6362; McKinnon et al. (1991), *J Mol Endocrinol* 6:231-239; Wood et al. (1990), *J. Immunol.* 145:3011-3016). The dihydrofolate reductase (DHFR)-deficient mutant cell lines (Urlaub et al. (1980), *Proc Natl Acad Sci USA* 77: 4216-4220), DXB11 and DG-44, are desirable CHO host cell lines because the efficient DHFR selectable and amplifiable gene expression system allows high level recombinant protein expression in these cells (Kaufman R. J. (1990), *Meth Enzymol* 185:537-566). In addition, these cells are easy to manipulate as adherent or suspension cultures and exhibit relatively good genetic stability. CHO cells and proteins recombinantly expressed in them have been extensively characterized and have been approved for use in clinical commercial manufacturing by regulatory agencies.

The methods of the invention can be used to culture cells that express recombinant proteins of interest. The expressed recombinant proteins may be secreted into the culture medium from which they can be recovered and/or collected. In addition, the proteins can be purified, or partially purified, from such culture or component (e.g., from culture medium) using known processes and products available from commercial vendors. The purified proteins can then be "formulated", meaning buffer exchanged, sterilized, bulk-packaged, and/or packaged for a final user. Suitable formulations for pharmaceutical compositions include those described in *Remington's Pharmaceutical Sciences,* 18th ed. 1995, Mack Publishing Company, Easton, Pa.

As used herein "peptide," "polypeptide" and "protein" are used interchangeably throughout and refer to a molecule comprising two or more amino acid residues joined to each other by peptide bonds. Peptides, polypeptides and proteins are also inclusive of modifications including, but not limited to, glycosylation, lipid attachment, sulfation, gamma-carboxylation of glutamic acid residues, hydroxylation and ADP-ribosylation. Polypeptides can be of scientific or commercial interest, including protein-based drugs. Polypeptides include, among other things, antibodies, fusion proteins, and cytokines. Peptides, polypeptides and proteins are produced by recombinant animal cell lines using cell culture methods and may be referred to as "recombinant peptide", "recombinant polypeptide" and "recombinant protein". The expressed protein(s) may be produced intracellularly or secreted into the culture medium from which it can be recovered and/or collected.

Examples of polypeptides that can be produced with the methods of the invention include proteins comprising amino acid sequences identical to or substantially similar to all or part of one of the following proteins: tumor necrosis factor (TNF), flt3 ligand (WO 94/28391), erythropoeitin, thrombopoeitin, calcitonin, IL-2, angiopoietin-2 (Maisonpierre et al. (1997), *Science* 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM_00682; Rüegg and Pytela (1995), *Gene* 160:257-62) growth hormone, insulin, insulinotropin, insulin-like growth factors, parathyroid hormone, interferons including α-interferons, γ-interferon, and consensus interferons (U.S. Pat. Nos. 4,695,623 and 4,897471), nerve growth factor, brain-derived neurotrophic factor, synaptotagmin-like proteins (SLP 1-5), neurotrophin-3, glucagon, interleukins, colony stimulating factors, lymphotoxin-β, leukemia inhibitory factor, and oncostatin-M. Descriptions of proteins that can be produced according to the inventive methods may be found in, for example, *Human Cytokines: Handbook for Basic and Clinical Research, all volumes* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook, Vols. 1 and 2* (Thompson and Lotze eds., Academic Press, San Diego, Calif., 2003).

Additionally the methods of the invention would be useful to produce proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. Nos. 5,395,760 and 5,610,279), Interleukin-1 (IL-1) receptors (types I and II; EP Patent No. 0460846, U.S. Pat. Nos. 4,968,607, and 5,767,064), IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other proteins that can be produced using the invention include proteins comprising all or part of the amino acid sequences of differentiation antigens (referred to as CD proteins) or their ligands or proteins substantially similar to either of these. Such antigens are disclosed in *Leukocyte Typing VI* (*Proceedings of the VIth International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be produced using the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

The term "antibody" includes reference to both glycosylated and non-glycosylated immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof. Also included are proteins having an antigen binding fragment or region such as Fab, Fab', F(ab')$_2$, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), *Cytokine Growth Factor Rev.* 13(1): 19-25), C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphlycoccus aureus*. Specific examples of known antibodies which can be produced using the methods of the invention include but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, vedolizumab, zalutumumab, and zanolimumab.

The invention can also be used to produce recombinant fusion proteins comprising, for example, any of the above-mentioned proteins. For example, recombinant fusion proteins comprising one of the above-mentioned proteins plus a multimerization domain, such as a leucine zipper, a coiled coil, an Fc portion of an immunoglobulin, or a substantially similar protein, can be produced using the methods of the invention. See e.g. WO94/10308; Lovejoy et al. (1993), *Science* 259:1288-1293; Harbury et al. (1993), *Science* 262:1401-05; Harbury et al. (1994), *Nature* 371:80-83; Håkansson et al. (1999), *Structure* 7:255-64. Specifically included among such recombinant fusion proteins are proteins in which a portion of a receptor is fused to an Fc portion of an antibody such as etanercept (a p75 TNFR:Fc), and belatacept (CTLA4:Fc).

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). All documents, or portions of documents, cited in this application, including but not limited to patents, patent applications, articles, books, and treatises, are hereby expressly incorporated by reference. What is described in an embodiment of the invention can be combined with other embodiments of the invention.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

Example 1

This experiment compares different start up conditions using batch or fed batch feeding methods followed by continuous perfusion using alternating tangential flow filtration. Perfusion was started either early during the early exponential growth phase ("batch" start up) with no additional feeds prior to perfusion or at the end of the exponential phase and entering into the stationary or production phase ("fed-batch" start up) receiving several bolus feeds of a serum-free defined feed media prior to perfusion.

On day 0, CHO cells expressing a recombinant antibody were inoculated into 2 L production bioreactors at $1 \times 10^6$ viable cells/mL in a working volume of 1500 ml of a serum-free defined medium for the fed-batch start and 1800 mL for the batch start. Cultures were maintained at 36° C., dissolved oxygen (DO) at 30%, agitation at 215 RPM. Glucose was maintained above 0 g/L and below 8 g/L.

Perfusion was started on day 4 (0.25 Vol/day) for the batch cultures and on day 7 (0.75 Vol/day) for the fed-batch cultures. Perfusion was accomplished using an alternating tangential flow perfusion and filtration system (Refine Technologies, Hanover, N.J., 50 kDa hollow fiber filter). Prior to starting perfusion the fed-batch cultures received bolus feeds of a concentrated serum-free defined feed media on day 4 (7.5% of initial working volume) and day 6 (10% initial working volume). Perfusion rates are provided in Table 1.

TABLE 1

Perfusion Rate

| Day | Perfusion Rate (Vol/day) |
|---|---|
| 0-4* | 0.00 |
| 4-6 | 0.25 |
| 6-7 | 0.50 |
| 7-10 | 0.75 |
| 10- | 1.00 |

Values are based on working volumes disclosed above
*Day 0-7 for the fed batch start During the culture run, daily samples were taken to assess the culture. Viable cell density (VCD) and viability were determined using Vi-Cell (Beckman Coulter, Brea, Calif.). Titer was measured by HPLC analysis. Packed cell volume was determined using VoluPAC (Sartorius, Goettingen, Germany).

A temperature shift (36.0° C. to 33.0° C.) was applied when the viable cell density exceeded $20 \times 10^6$ viable cells/mL which was day 7 and day 11 for the batch and fed-batch start conditions respectively.

Figure 1B:
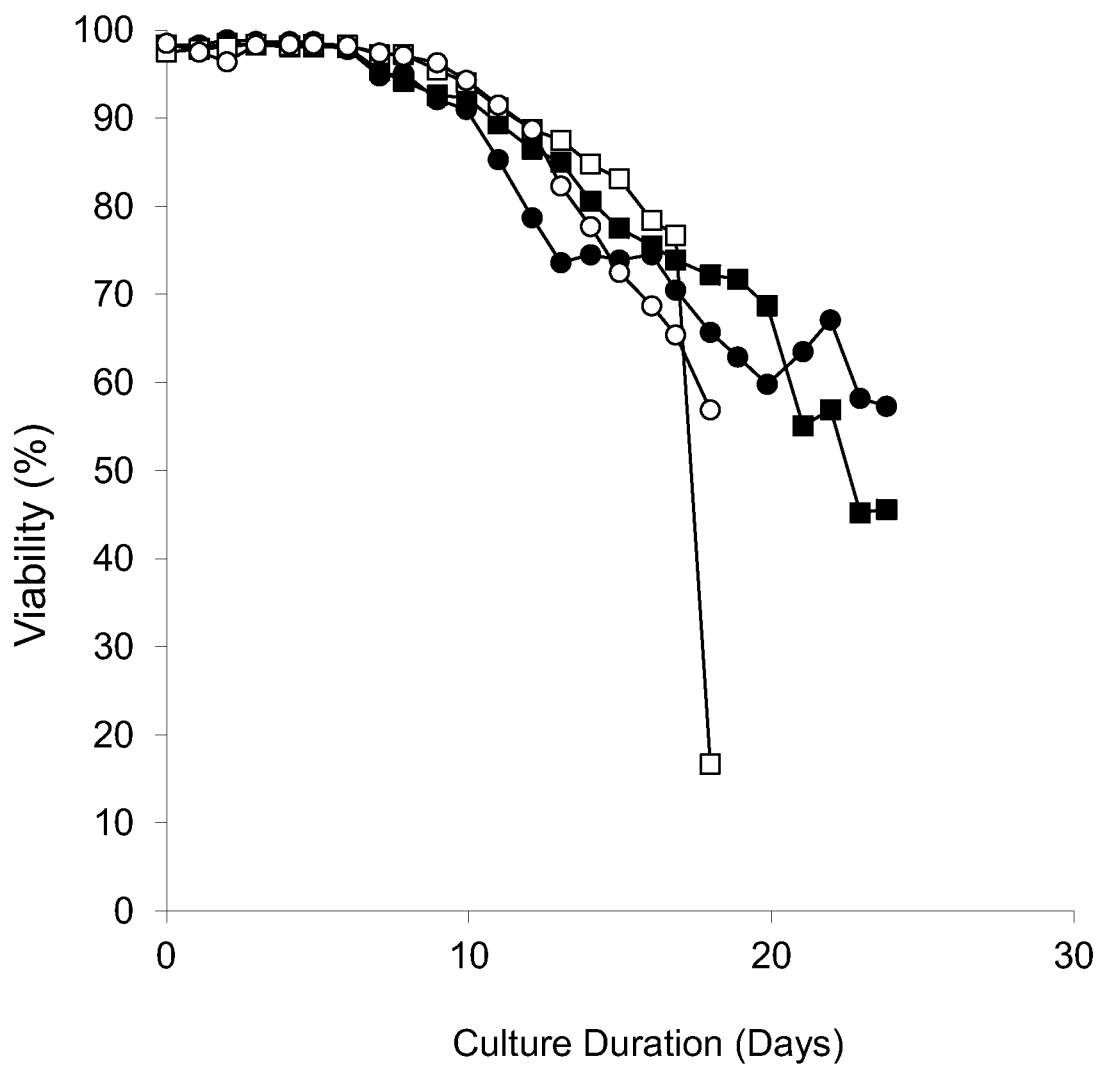
FIG. 1B: Viability.
Figure 1C:
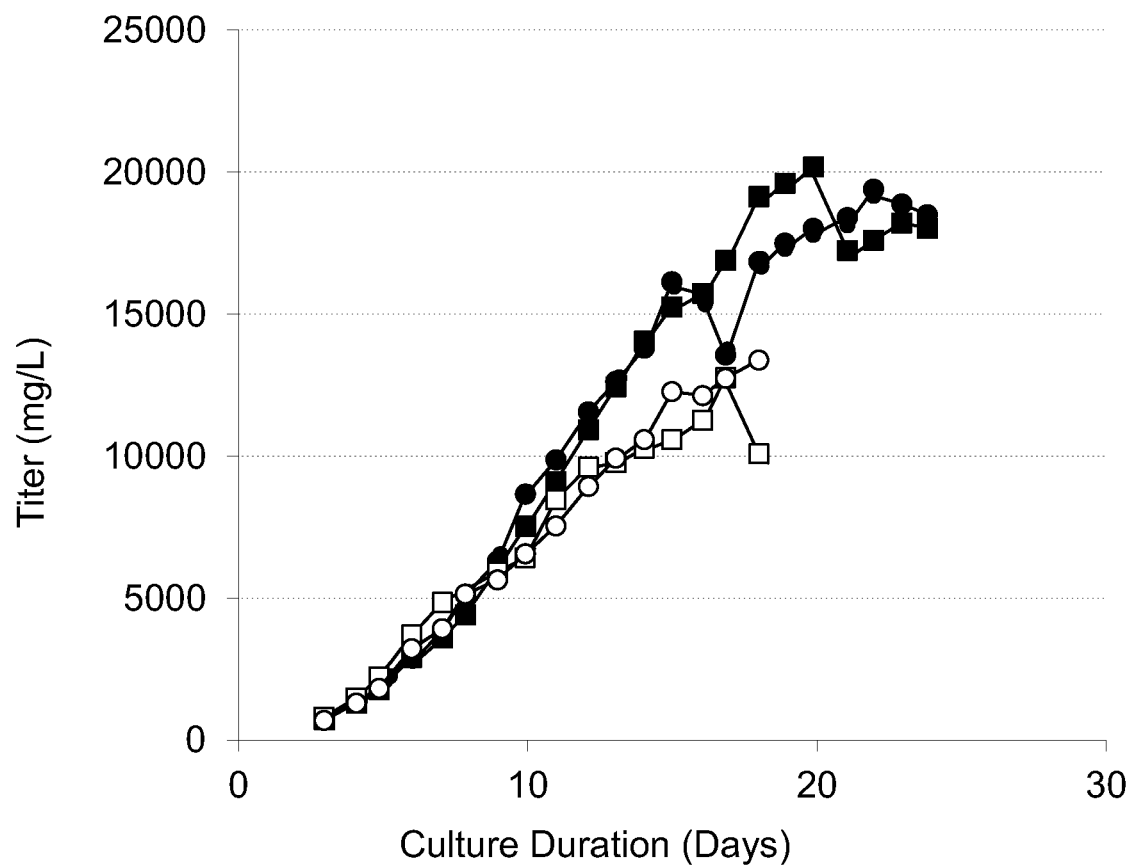
FIG. 1C: Titer

For the batch start-up conditions, the viable cell density continued to increase after the perfusion was started; for the fed-batch start conditions, the perfusion was started after the cell culture had reached a plateau or stationary phase with little growth. On day 15, the viable cell density for the fed batch was between 27.7 and $30.7 \times 10^6$ viable cells/mL while VCD of the batch culture was between 22.5 and $27.4 \times 10^6$ viable cells/mL (FIG. 1A). Viability of the fed batch culture was between 73.9 and 77.5% while the batch culture viability was between 72.5 and 83.1% (FIG. 1B). The titer of the fed batch culture was between 15.3 and 16.1 g/L while the batch culture titer was between 10.6 and 12.3 g/L (FIG. 1C). Since the integrated variable cell density (IVCD) values were similar for all four cultures by day 15 (approximately $230 \times 10^6$ cell days/mL), the specific productivity was higher in the fed-batch start-up conditions. The fed batch cultures were continued to day 24. A titer of 20 g/L was achieved at 20 days.

The alternating tangential flow perfusion with a fed batch start-up resulted in increased productivity, maintaining the cells in a more productive state compared to the batch start method.

Example 2

On day 0, CHO cells expressing a recombinant antibody were inoculated into 2 L production bioreactors at $1 \times 10^6$ viable cells/mL in a working volume of 1500 ml of a serum-free defined medium for the batch start and 1300 mL for the fed-batch start. Cultures were maintained at 36° C., DO at 30%, agitation at 215 RPM for batch cultures. The fed-batch culture was agitated at 430 RPM. Fed-batch culture was fed to 7 g/L glucose daily prior to perfusion and all cultures were maintained at or above 4 g/L glucose during perfusion. Perfusion (alternating tangential flow) was started on day 4 (0.25 Vol/day) for the batch cultures and on day 8 (0.75 Vol/day) for the fed-batch culture. Prior to starting perfusion the fed-batch culture received bolus feeds of a concentrated serum-free defined feed media on day 4 (7.5% of initial working volume) and day 6 (10% initial working volume). Perfusion flow rates settings are provided in Table 2. The cultures were maintained for 21 days.

TABLE 2

Perfusion Rate

| Day | Perfusion Rate (Vol/day) |
|---|---|
| 4-6 | 0.25 |
| 6-8 | 0.50 |
| 8-10 | 0.75 |
| 10- | 1.00 |

Values are based on working volumes disclosed above

During the culture run daily samples were taken as described above to assess the culture.

A temperature shift (36.0° C. to 33.0° C.) was applied to the batch cultures on day 6 when the viable cell density exceeded $20 \times 10^6$ viable cells/mL, as in Example 1. The fed batch culture was maintained at 36.0° C. for the duration of the culture.

Figure 2A:
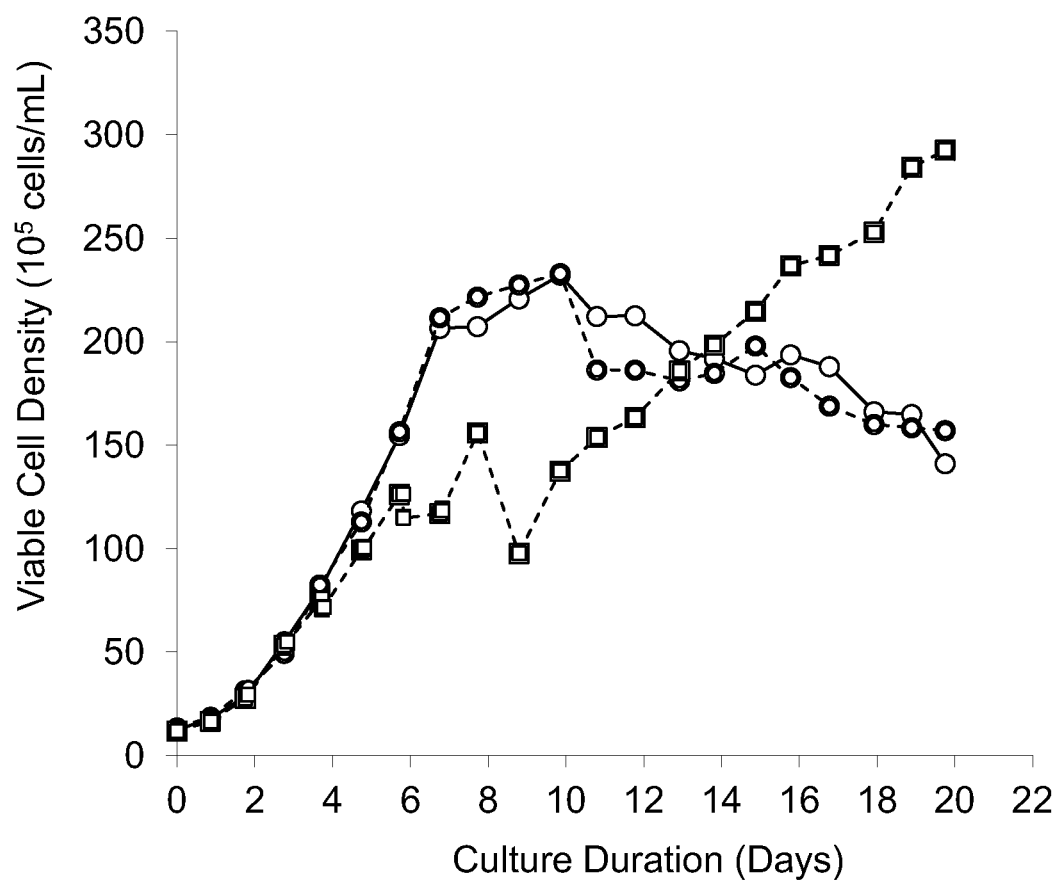
FIG. 2A Viable cell density, FIG. 2B Viability, FIG. 2C Titer, FIG. 2D Asparagine concentration FIG. 3 1.0 start perfusion volume, no temperature shift: solid circle. 1.0 start perfusion volume, temperature shift: open circle (○). 0.75 start perfusion volume perfusion volume, no temperature shift: solid square (θ). 0.75 start perfusion volume, temperature shift: open square (□).
Figure 2B:
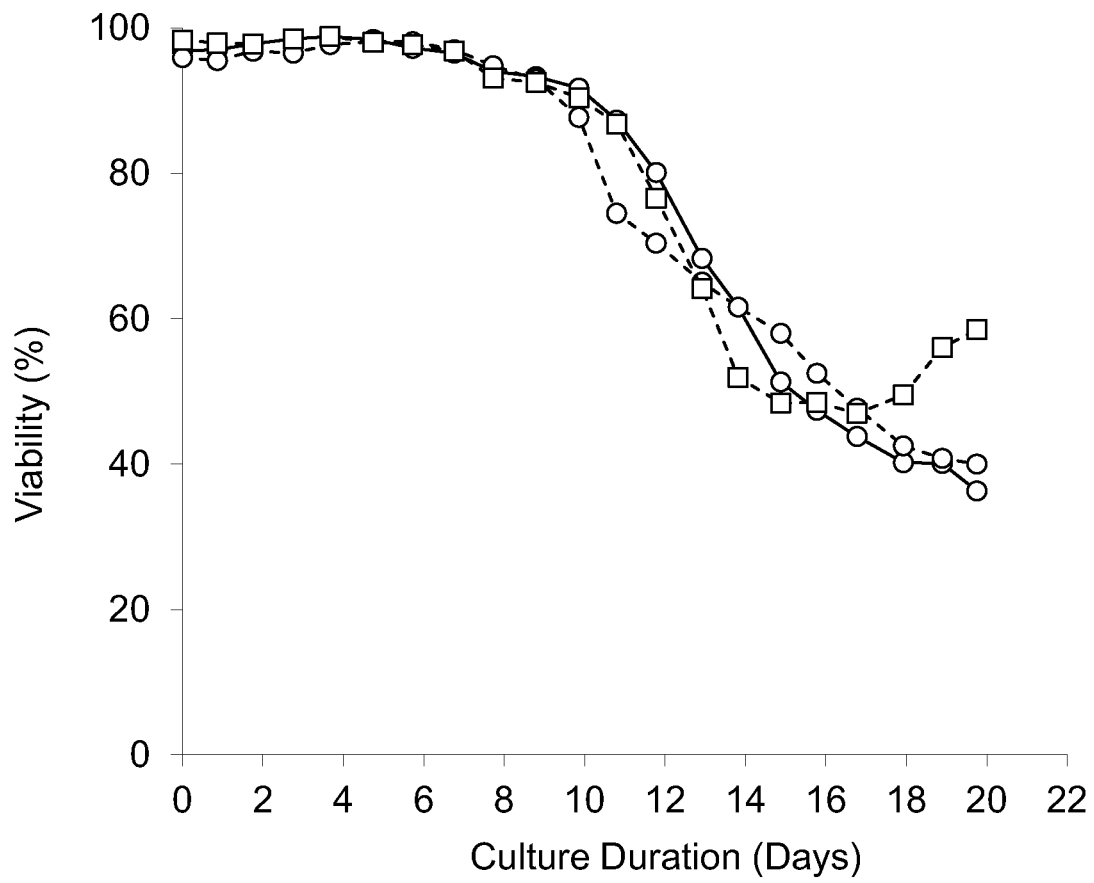
FIG. 2 Batch start: open circle (○), Fed-batch start with high agitation: open square (□)
Figure 2C:
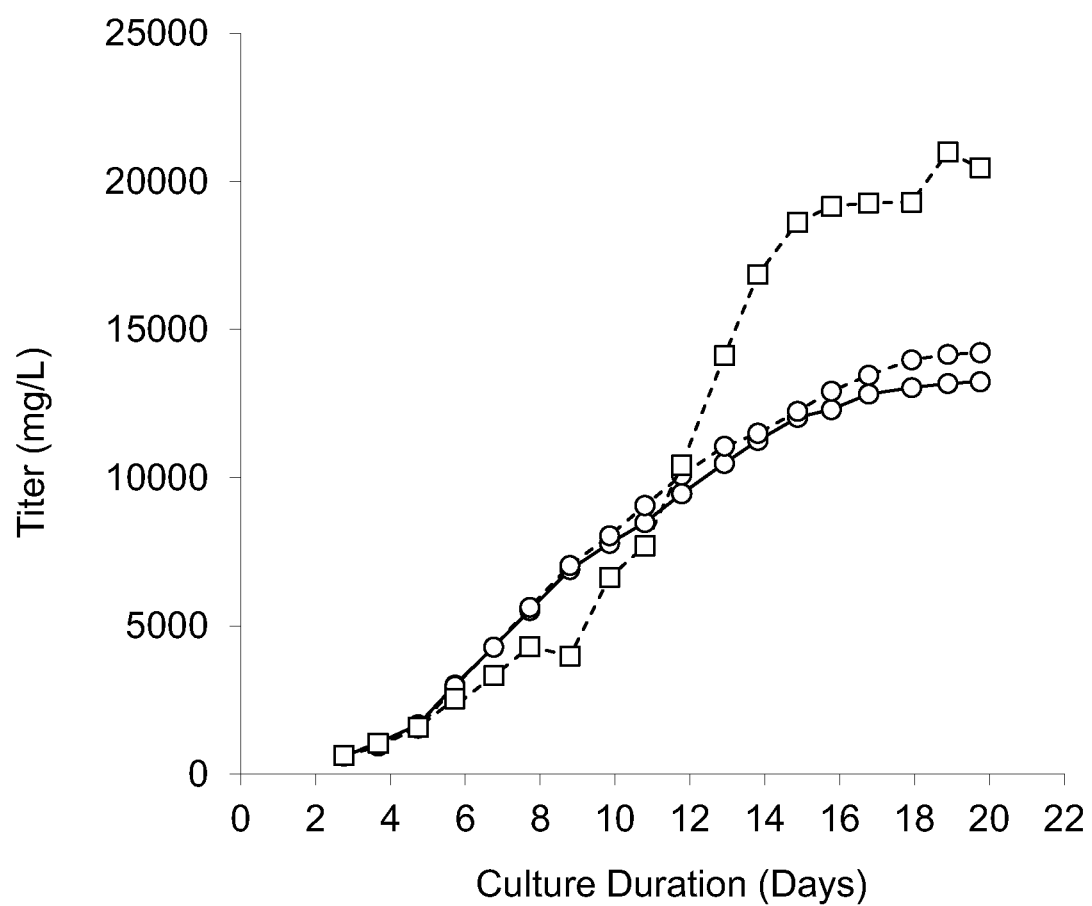
Figure 2D:
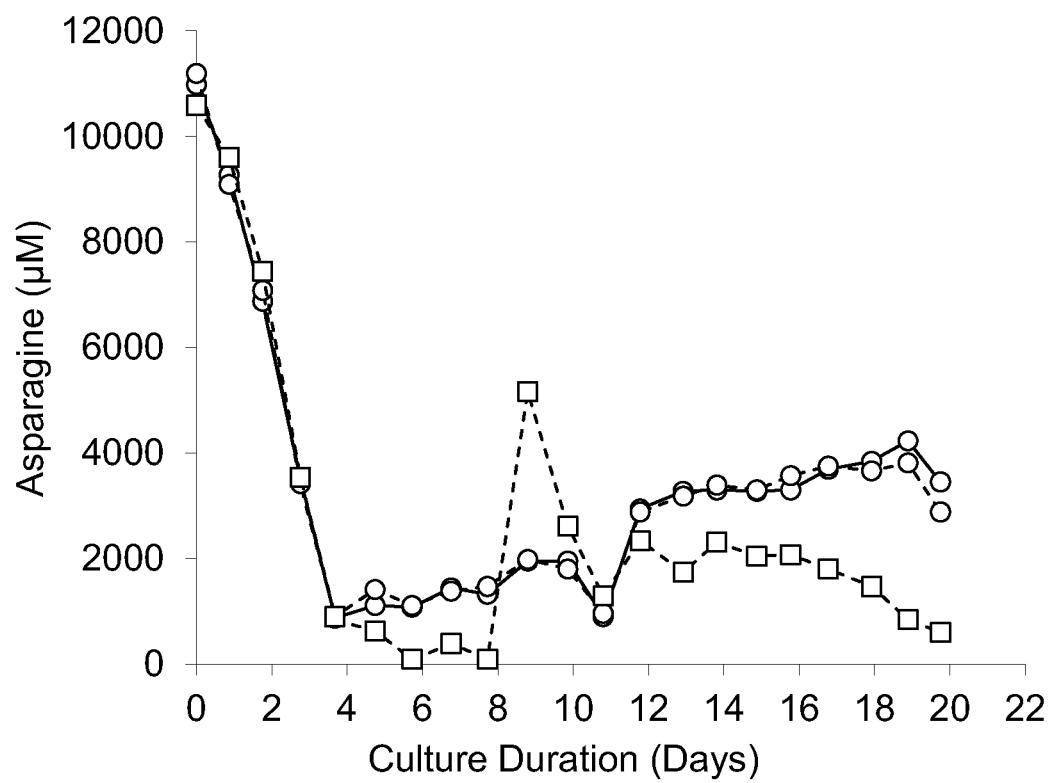

The batch start-up method cultures had results similar to those described above with the cells reaching approximately 20 to $25 \times 10^6$ viable cells/mL with no growth after day 10. The fed-batch culture reached almost $30 \times 10^6$ viable cells/mL on day 20 after spending most of the culture duration below $20 \times 10^6$ viable cells/mL, see FIG. 2A. The viabilities all remained above 80% until day 10 and then dropping to about 40% by day 20 for the batch start cultures and 60% for the fed-batch culture, see FIG. 2B. The titer peaked at almost 15 g/L for the batch start cultures, but it reached over 20 g/L for the high agitation fed-batch culture, see FIG. 2C. It was observed that the batch start cultures had an L-asparagine concentration of about 3 to 4 mM on day 3, and did not experience an asparagine limited culture environment. However, the fed-batch perfusion start culture experienced an L-asparagine limited environment by day 6 prior to the start of the perfusion on day 7. The culture was then perfused with medium containing L-asparagine at a concentration of 2.0 g/L (or 13.3 mM) that resulted in no further L-asparagine limitations after day 8 (FIG. 2D). Glucose concentrations were maintained mostly between 4 and 10 g/L.

The fed-batch start-up with high agitation perfusion culture achieved the highest titer (over 20 g/L) in 20 days, more than 5 g/L higher than the batch start-up cultures, which was similar to the results described above. No negative effects of a higher agitation rate were observed. Maintaining a constant temperature did not appear to negatively impact the fed batch culture.

Example 3

This experiment characterizes the effects of perfusion volume and temperature shifts on an alternating tangential flow perfusion with a fed batch start-up as described above. All cultures were fed-batch start with perfusion beginning on day 7. Perfusion flow rates moving from three-quarter working volumes to full volume or from full working volume to three-quarter working volume were tested. A temperature shift from 36° C. to 33° C. on Day 14 was also tested.

On day 0, CHO cells expressing a recombinant antibody were inoculated into 2 L production bioreactors at $1 \times 10^6$ cells/mL in a working volume of 1200 ml of a serum-free defined medium. Cultures were maintained at 36° C., DO at 30%. Prior to perfusion, glucose was fed to 7 g/L daily and during perfusion glucose was maintained above 1 g/L. The culture was maintained for 20 days.

Cultures received bolus feeds of a concentrated serum-free defined feed media on day 4 (7.5% of initial working volume) and day 6 (10% initial working volume). Perfusion began on Day 8. Perfusion rates are provided in Table 3. One culture from each group had a temperature shift from 36° C. to 33° C. on Day 15, the other cultures remained at 36° C. for the duration of the experiment

TABLE 3

| | Perfusion Rate | |
|---|---|---|
| Condition | Day | Perfusion Rate (Vol/day) |
| Condition 1 | 8-12 | 0.75 |
| (n = 2) | 12- | 1.00 |
| Condition 2 | 8-10 | 1.00 |
| (n = 2) | 10- | 0.75 |

Values are based on working volumes disclosed above

Figure 3A:
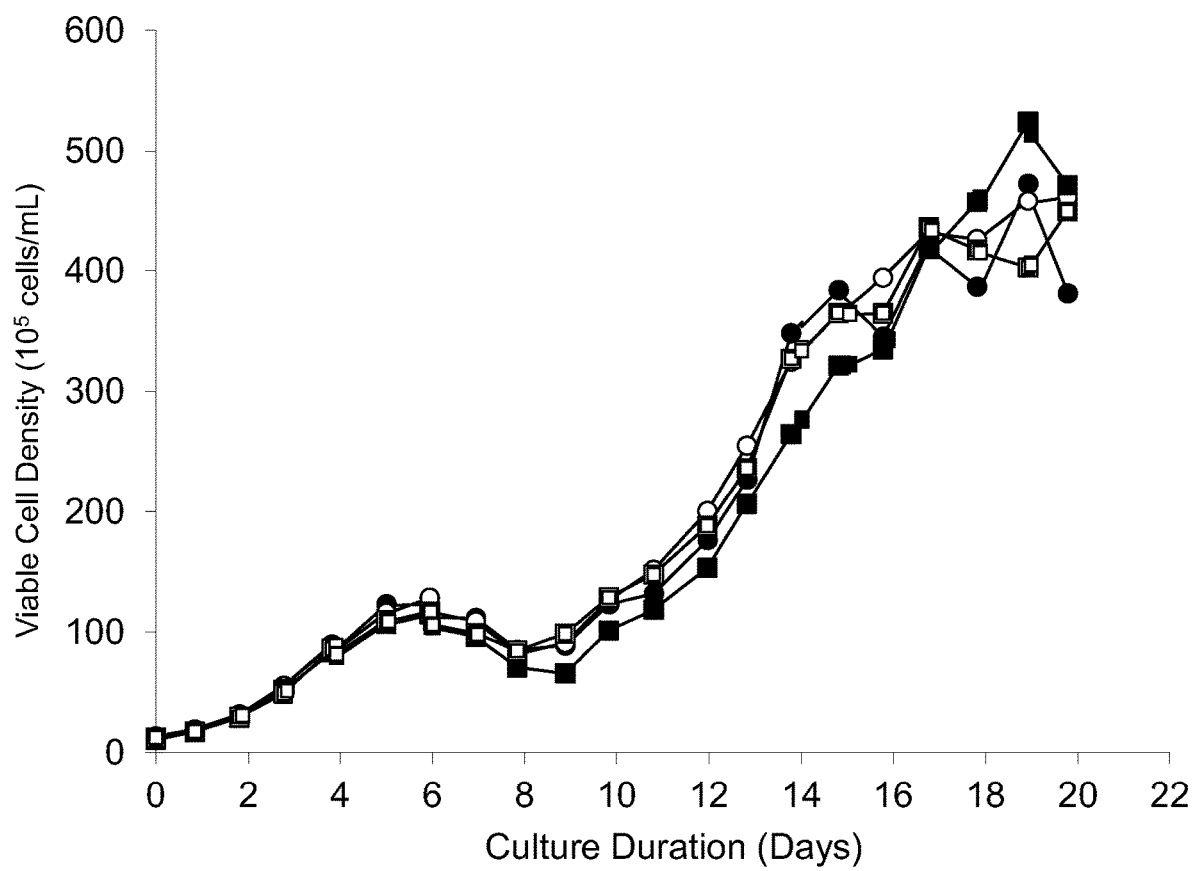
FIG. 3A Viable Cell Density, FIG. 3B Viability, FIG. 3C Titer
Figure 3B:
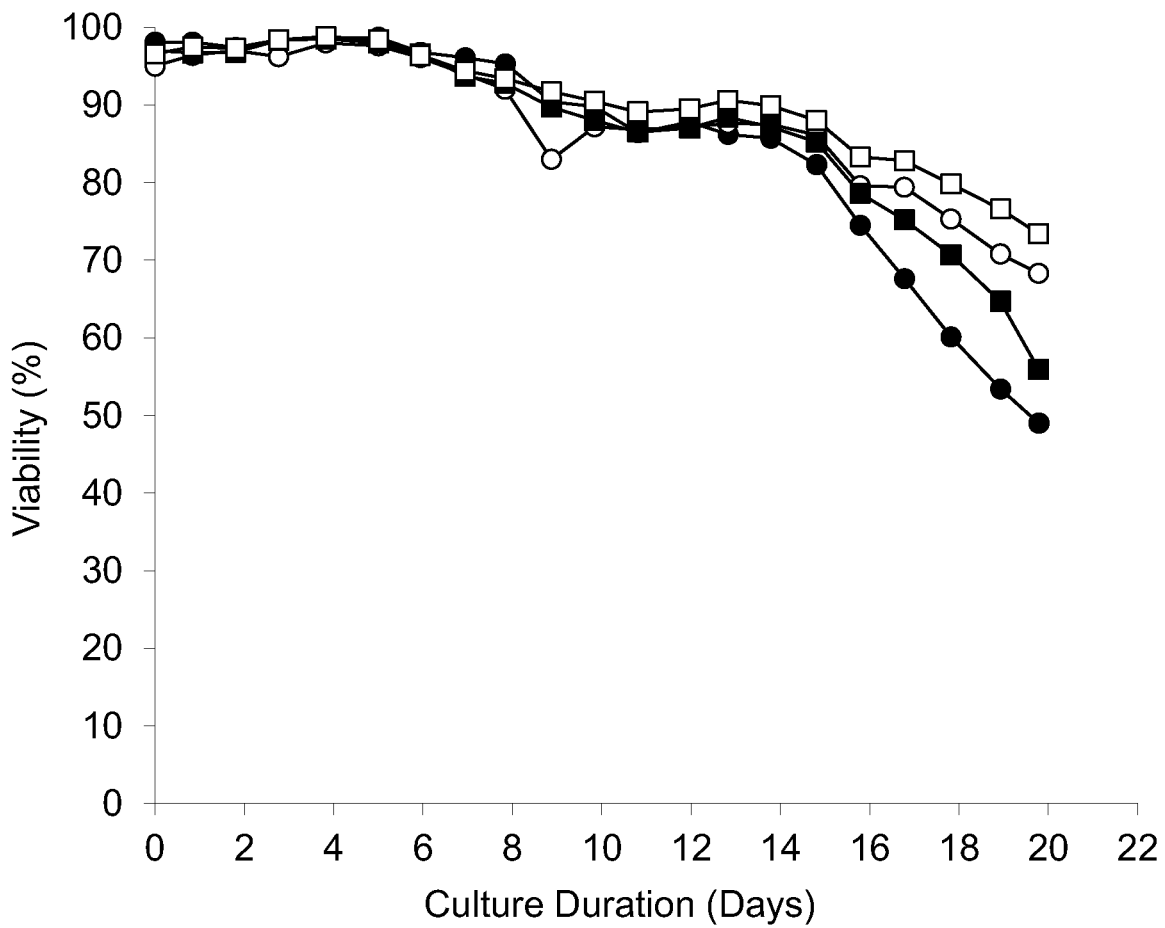
Figure 3C:
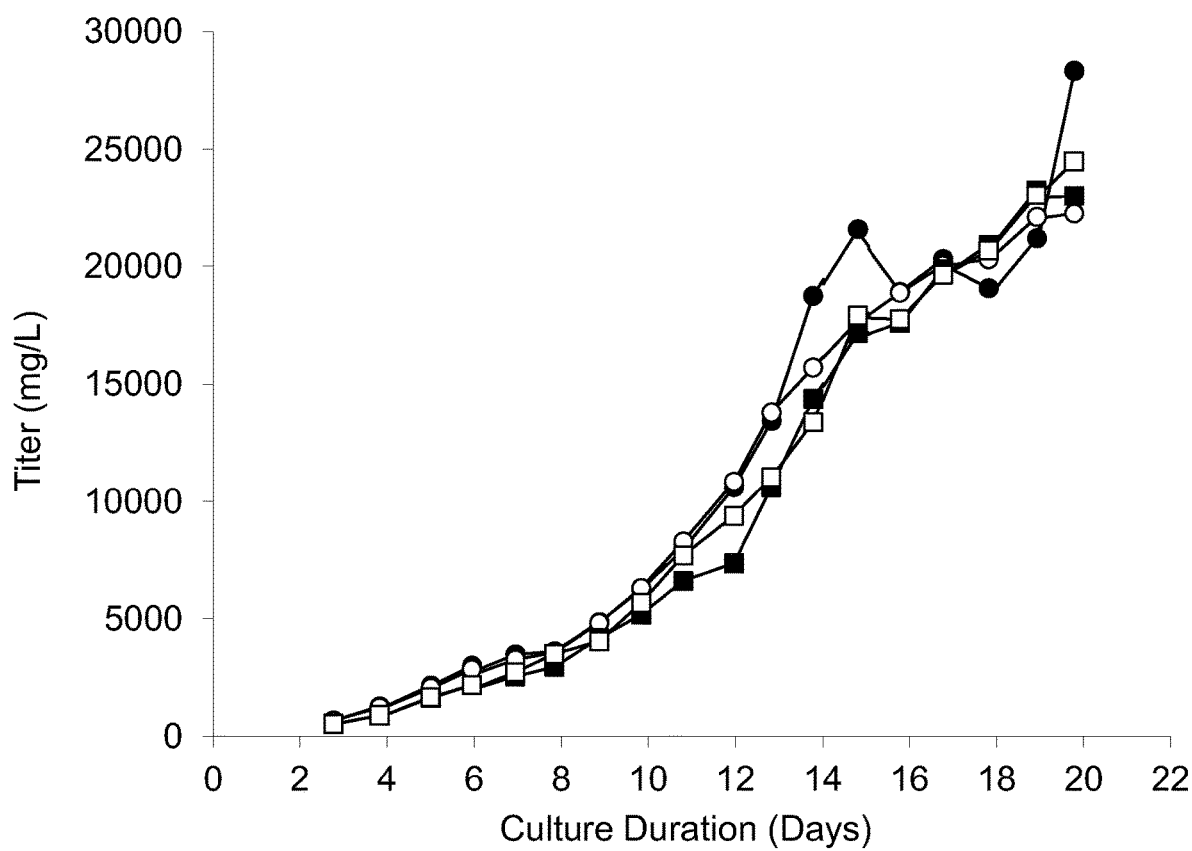

Temperature shift and perfusion rate did not impact viable cell density, see FIG. 3A. However, a temperature shift appears to help preserve viability at later time points in a culture. There appears to be a break out between the temperatures shift conditions starting on Day 15 onward. The viability of the temperature shifted cultures dropped more slowly than the cultures that remained at 36° C., see FIG. 3B. As for titer, three cultures showed very similar titers on Day 15 (17.1-17.9 g/L) as well as on Day 20 (22-24 g/L), but one culture had a higher titer on Day 15 (21.58 g/L) as well as on Day 20 (28.33 g/L) (see FIG. 3C). Neither the temperature nor perfusion rates appeared to have any impact on titer production, suggesting that cultures can be maintained with different perfusion rates.

Example 4

This experiment was designed to investigate the effects of perfusion medium asparagine concentrations and perfusion start conditions with either L-asparagine limited or non-limited culture environments on viable cell density during the production phase.

On day 0, CHO cells expressing a recombinant antibody were inoculated into 2 L production bioreactors at 1×10$^6$ cells/mL in a working volume of 1500 ml for both the batch and fed-batch start methods. Cultures were maintained at 36° C., dissolved oxygen (DO) at 30%, agitation at 400 RPM. Sparging was done using either a drilled pipe or a sintered sparger. Glucose was maintained above 0 g/L and below 8 g/L.

Perfusion (alternating tangential flow) was started on day 3 (0.29 Vol/day) for the batch start "non-asparagine-limited cultures" and on day 7 (0.48 Vol/day) for the fed-batch "asparagine-limited cultures". The batch culture medium contained 10 mM L-asparagine. Prior to starting perfusion the fed-batch cultures received bolus feeds of a concentrated serum-free defined feed media on days 3 and 6 (7% initial working volume) containing 113.4 mM L-asparagine. Perfusion medium asparagine concentrations were either at a control concentration (17.3 mM Asn in a serum free defined perfusion medium) or a low concentration (5 mM Asn in a serum free defined perfusion medium). Perfusion was carried out as described above. Perfusion rates are provided in Table 4.

TABLE 4

| | Perfusion Rates | |
|---|---|---|
| Condition | Day | Perfusion Rate (Vol/day) |
| Day 3 | 3-4 | 0.29 |
| Batch | 4-7 | 0.48 |
| Perfusion Start | 7-9 | 0.48 |
| non-asparagine- | 9-11 | 0.67 |
| limited culture | 11-20 | 0.96 |
| Day 7 | 7-9 | 0.48 |
| Fed-Batch Perfusion | 9-11 | 0.67 |
| Start | | |
| asparagine-limited | 11-20 | 0.96 |
| culture | | |

During the culture run, daily samples were taken to assess the culture. Viable cell density (VCD) and viability were determined using Vi-Cell (Beckman Coulter, Brea, Calif.). Titer was measured by HPLC analysis. All cultures were maintained at 36.0° C.

Figure 4A:
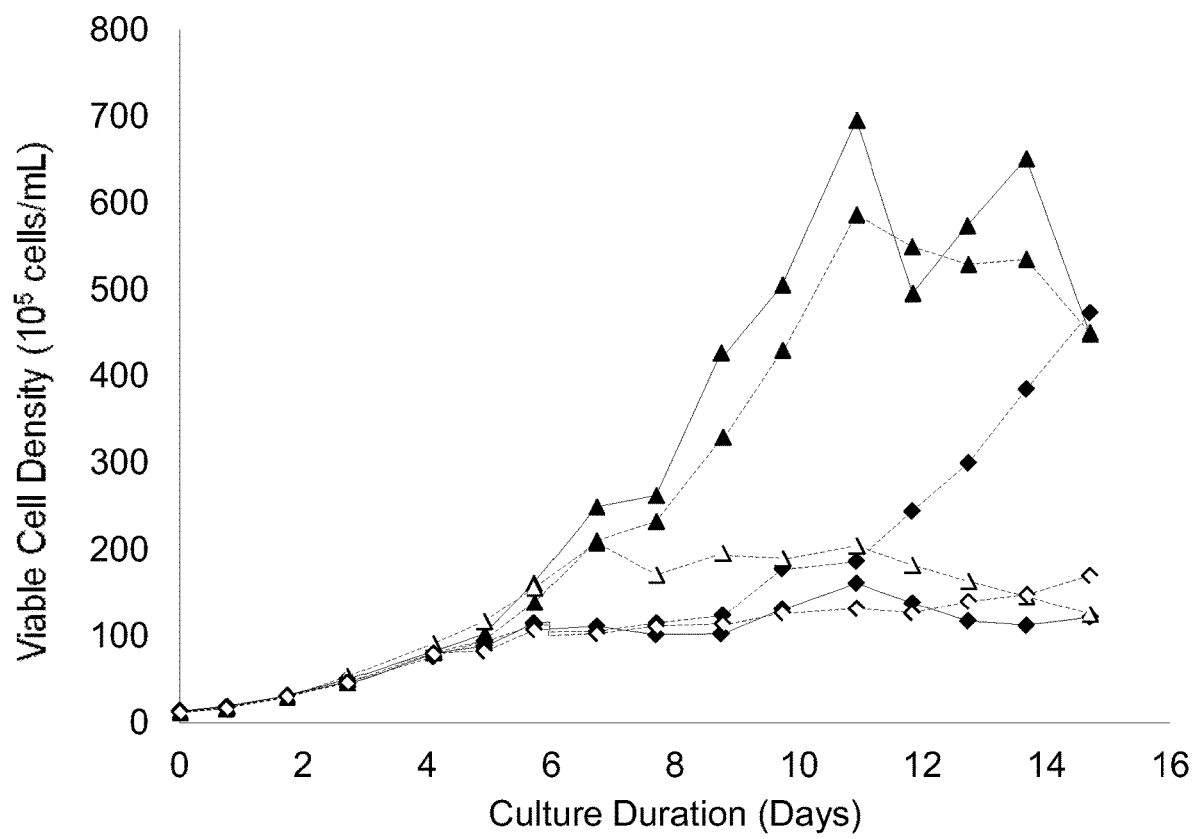
FIG. 4A Viable Cell Density, FIG. 4B Viability, FIG. 4C PCV Adjusted Titer
Figure 4B:
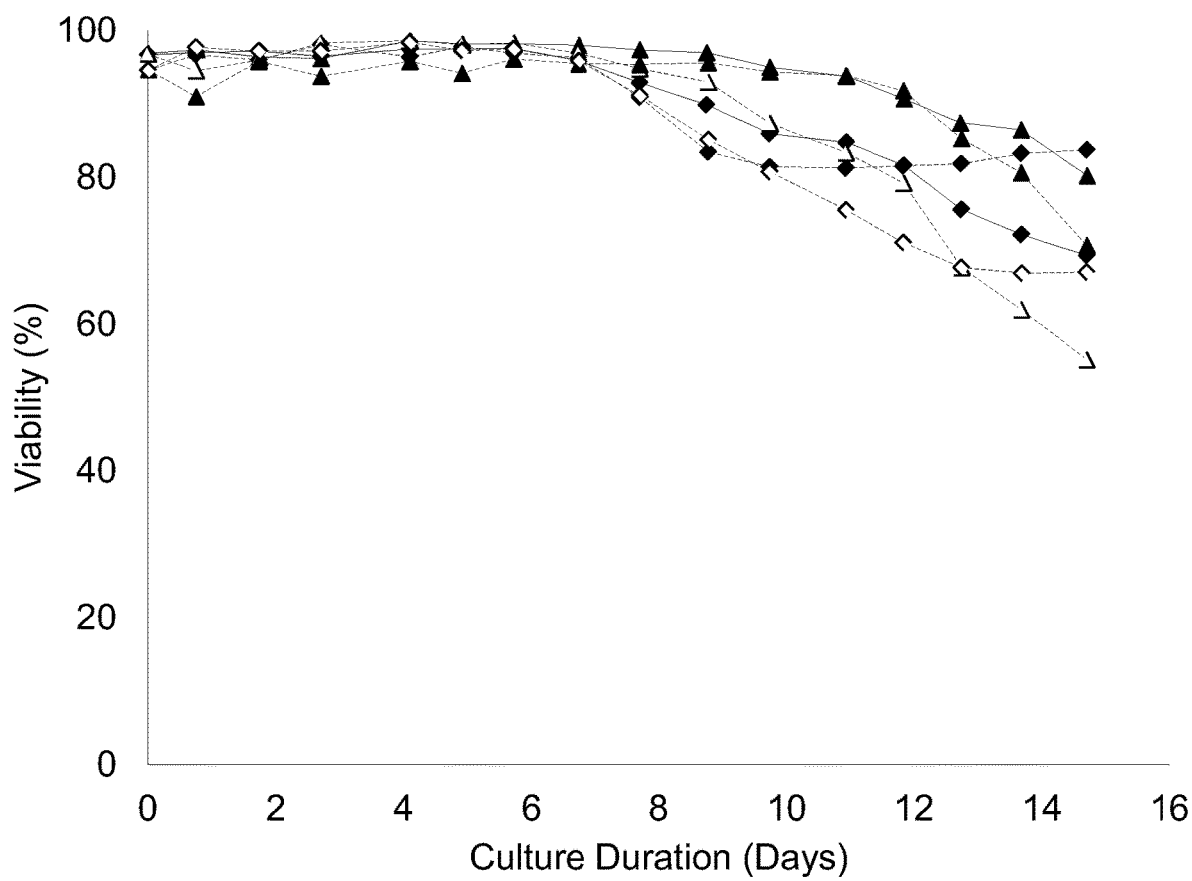
FIG. 4 Batch start with low asparagine amount: open triangle (Δ). Batch start with control L-asparagine amount: solid triangle (▲). Fed-batch start with low L-asparagine amount: open diamond (◇). Fed-batch start with control L-asparagine amount: solid diamond (◆). Sparge with drilled pipe: Solid line. Sparge with sintered sparger: dashed line.
Figure 4C:
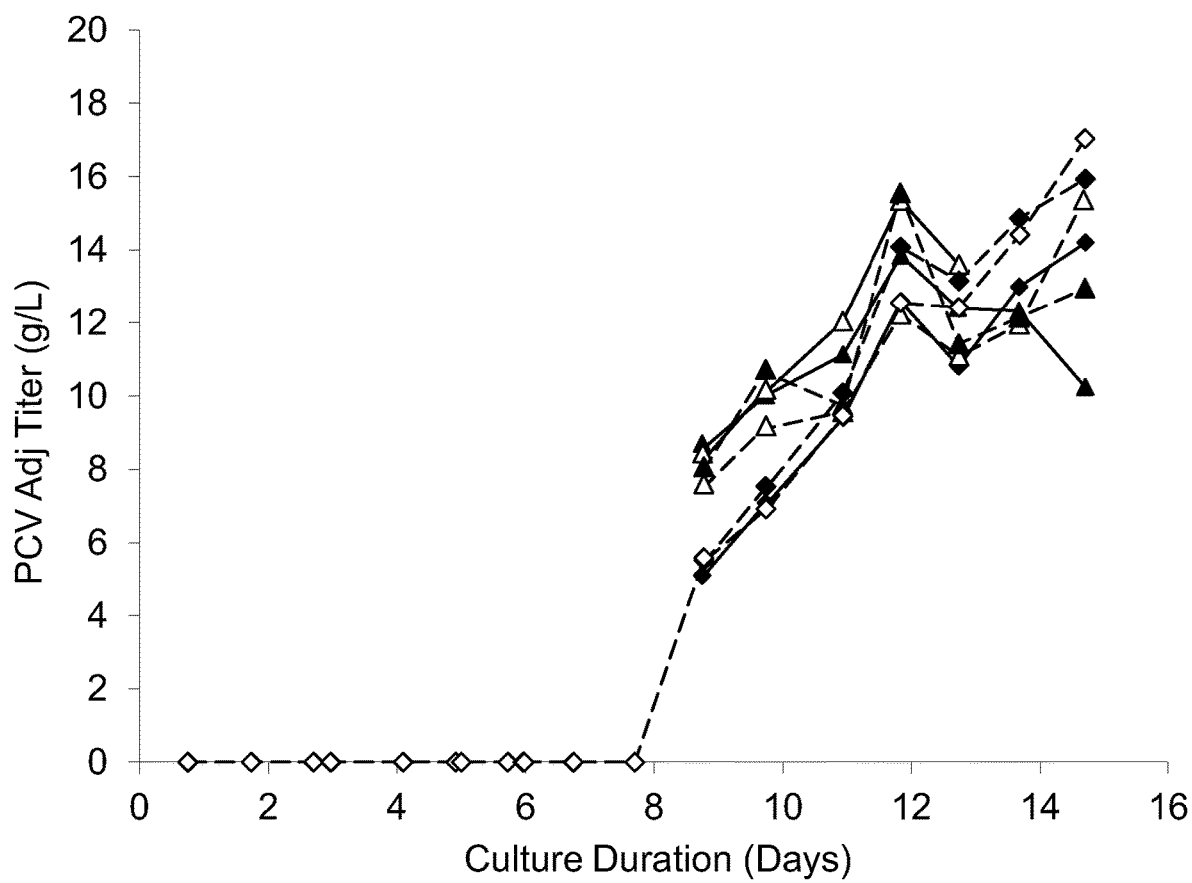

Reduction in cell growth and improved productivity was achieved during the production phase by limiting asparagine in the culture medium. On day 15, the maximum viable cell density was about 17.0×10$^6$ viable cells/mL for the fed-batch start cultures with low asparagine (FIG. 4A). Control level asparagine cultures reached viable cell densities exceeding 40×10$^6$ viable cells/mL (>30% packed cell volume). Viability of the low asparagine fed-batch culture was 67.1% while the batch culture viability was 55.1% and the control was 69% (FIG. 4B). The packed cell volume adjusted titer of the low asparagine fed-batch culture was 17.0 g/L (adjusted for packed cell volume) while the batch culture titer was between 15.4 g/L (FIG. 4C). The controls had titers of 10.2 to 12.9 g/L (batch start) and 14.2 to 15.9 g/L (fed-batch start).

Maintaining asparagine levels at 5 mM or less during the production resulted in growth-arrest, stimulated productivity and maintained viability during the production phase.

Example: 5

This experiment compares media conditions during perfusion. In this 2 L bioreactor experiment, cells were inoculated into a chemically defined batch medium at a working volume of 1.5 L, cultured for 3 days and then perfused for 12 days using a chemically defined perfusion medium containing either 17.3 mM L-asparagine and 4.6 mM L-glutamine or 5 mM L-asparagine and 10 mM L-glutamine. Perfusion was accomplished using an alternating tangential flow perfusion and filtration system (Refine Technologies, Hanover, N.J.) with a 30 kDa hollow fiber filter (GE Healthcare, Little Chalfont, UK). Perfusion was started on day 3 at a rate of 0.3 culture volumes per day. The rate of perfusion was increased on days 4, 9, and 11 as indicated in Table 6 below. Cultures were maintained at 36° C., DO at 30%, pH at 7.0, and agitation at 400 rpm.

During the culture run, daily samples were taken to assess the culture. Viable cell density (VCD) and viability were determined using Vi-Cell (Beckman Coulter, Brea, Calif.). Titer was measured by HPLC analysis. Packed cell volume was determined using VoluPAC (Sartorius, Goettingen, Germany).

TABLE 5

Perfusion rate schedule

| Day | Perfusion Rate (Vol/day) |
|---|---|
| 3 | 0.30 |
| 4 | 0.50 |
| 9 | 0.67 |
| 11 | 0.96 |

Figure 5A:
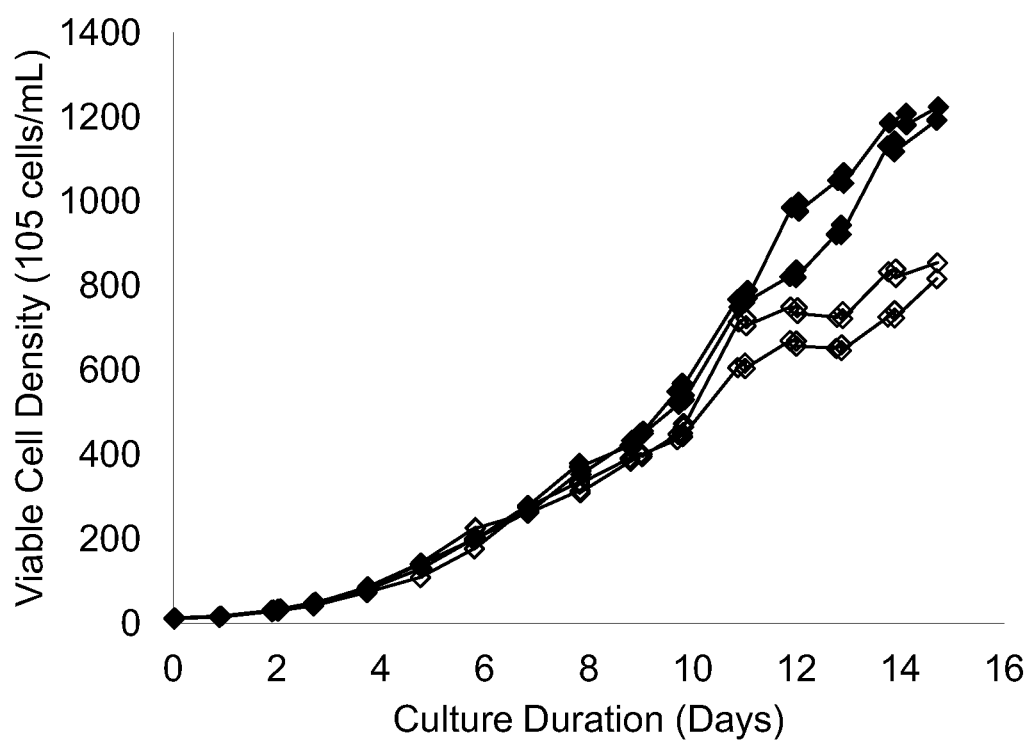
FIG. 5A Viable cell density.
Figure 5B:
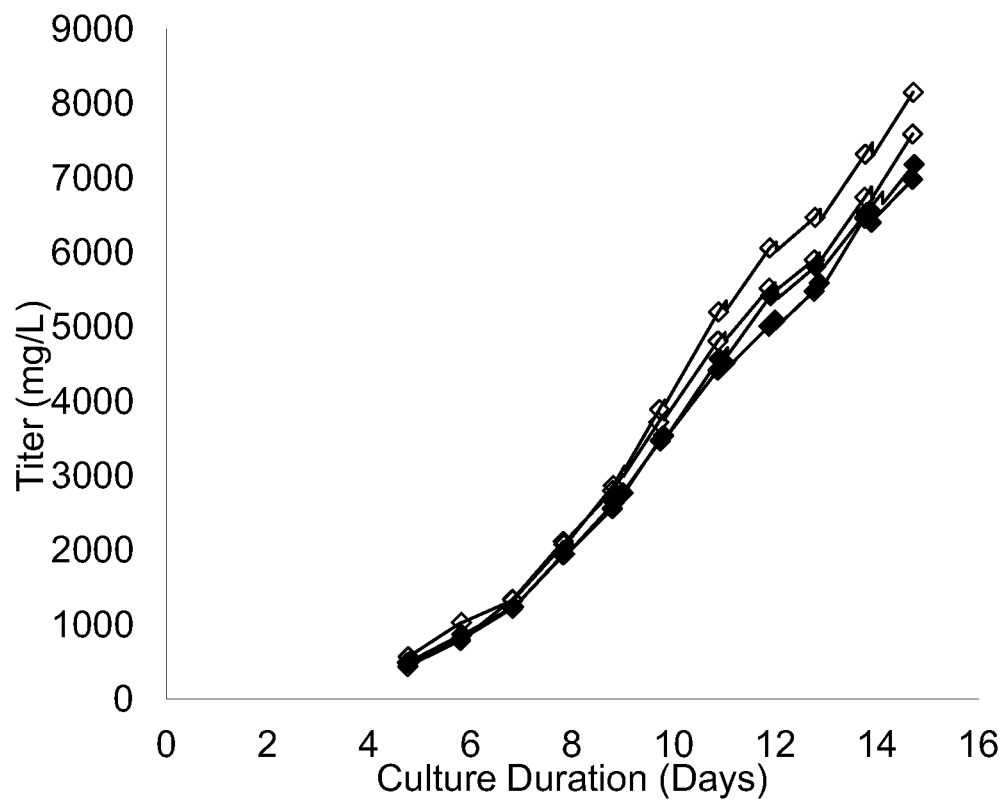
FIG. 5B Titer.
Figure 5C:
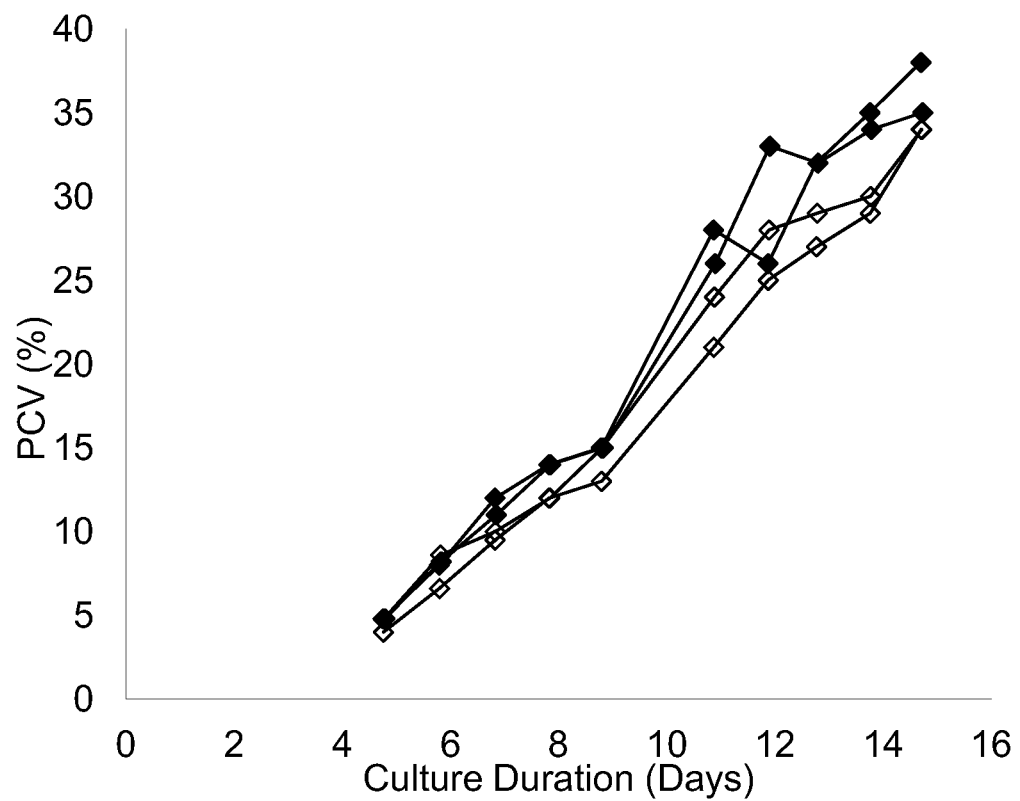
FIG. 5C Packed cell volume (PCV).
Figure 5D:
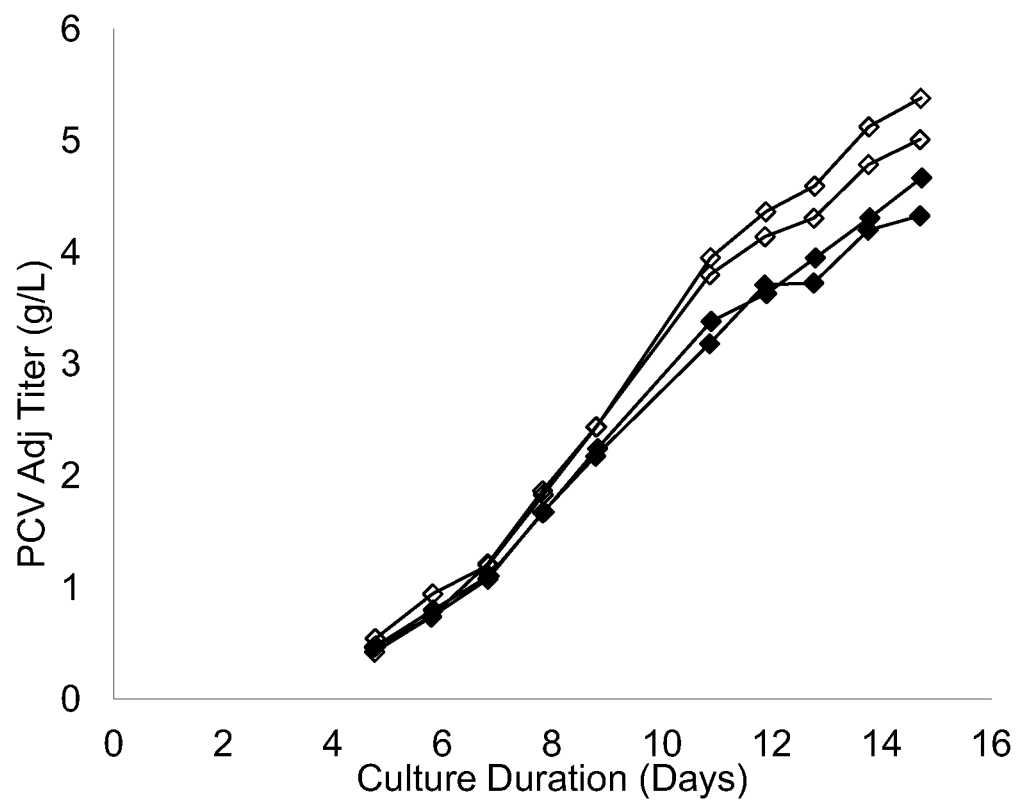
FIG. 5D PCV-adjusted titer.
Figure 5E:
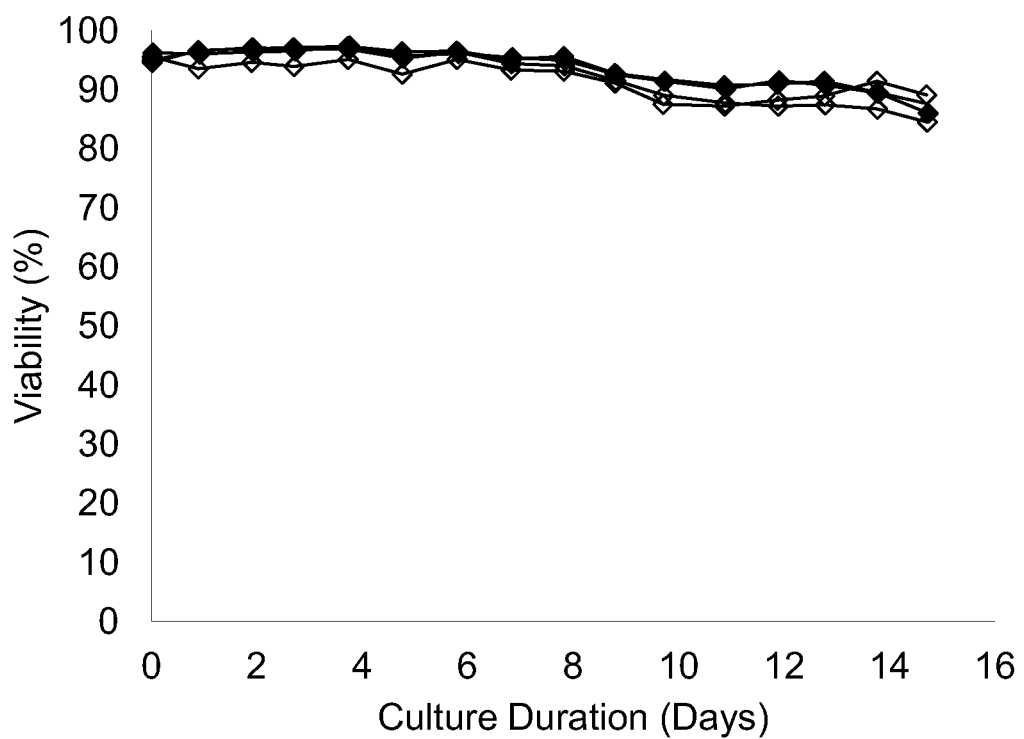
FIG. 5E Viability.

Asparagine limitation resulted in the accumulation of fewer cells and improved productivity. Cultures perfused with media containing 5 mM asparagine reached a maximum VCD of $8.16 \times 10^7$-$8.54 \times 10^7$ cells/mL while cultures perfused with media containing 17.3 mM asparagine reached $11.9 \times 10^7$-$12.2 \times 10^7$ cells/mL (FIG. 5A). Although the cultures in 17.3 mM asparagine had more cells, the cultures in 5 mM asparagine made more product. Cultures perfused with media containing 17.3 mM asparagine made 6.89-7.18 g/L (4.33-4.67 g/L packed cell volume adjusted) compared to 7.59-8.15 g/L (5.01-5.38 g/L packed cell volume adjusted) for cultures perfused with media containing 5 mM asparagine (FIGS. 5B and 5D). The final packed cell volume (PCV) of the 5 mM asparagine cultures trended slightly lower than the 17.3 mM asparagine cultures (FIG. 5C) and there was no difference in culture viability (FIG. 5E).

Interestingly, in this example increasing the concentration of glutamine by more than two-fold in the low-asparagine condition (4.6 mM versus 10 mM glutamine) did not interfere with the ability of the low-asparagine medium to arrest the growth of the culture.

Example 6

This example compares the performance of a clonal, antibody-expressing CHO cell line cultured in an ATF perfusion process using asparagine limitation to control growth at bench and pilot scales. The bench-scale model utilized 2 L bioreactors and the pilot scale was 500 L. At bench scale, cells were inoculated into a chemically defined batch medium at a working volume of 1.5 L and at pilot scale the working volume was about 378 L. Cells were cultured for 3 days in the batch medium and then perfused for 12 days using a chemically defined perfusion medium containing 5 mM L-asparagine and 10 mM L-glutamine. Perfusion was accomplished using an alternating tangential flow perfusion and filtration system (Refine Technologies, Hanover, N.J.) with a 30 kDa hollow fiber filter (GE Healthcare, Little Chalfont, UK). Perfusion was started on day 3 at a rate of 0.3 culture volumes per day. The rate of perfusion was increased on days 4, 9, and 11 as indicated in Table 7 below. Cultures were maintained at 36° C., 30% DO, and pH 6.9.

During the culture run, daily samples were taken to assess the culture. Viable cell density (VCD) and viability were determined bench scale using Vi-Cell (Beckman Coulter, Brea, Calif.) and at pilot scale using a CEDEX (Roche Applied Science, Indianapolis, Ind.). Titer was measured by HPLC analysis. Packed cell volume was determined using VoluPAC (Sartorius, Goettingen, Germany).

TABLE 6

Perfusion rate schedule

| Day | Perfusion Rate (Vol/day) |
|---|---|
| 3 | 0.30 |
| 4 | 0.50 |
| 9 | 0.67 |
| 11 | 0.96 |

Figure 6A:
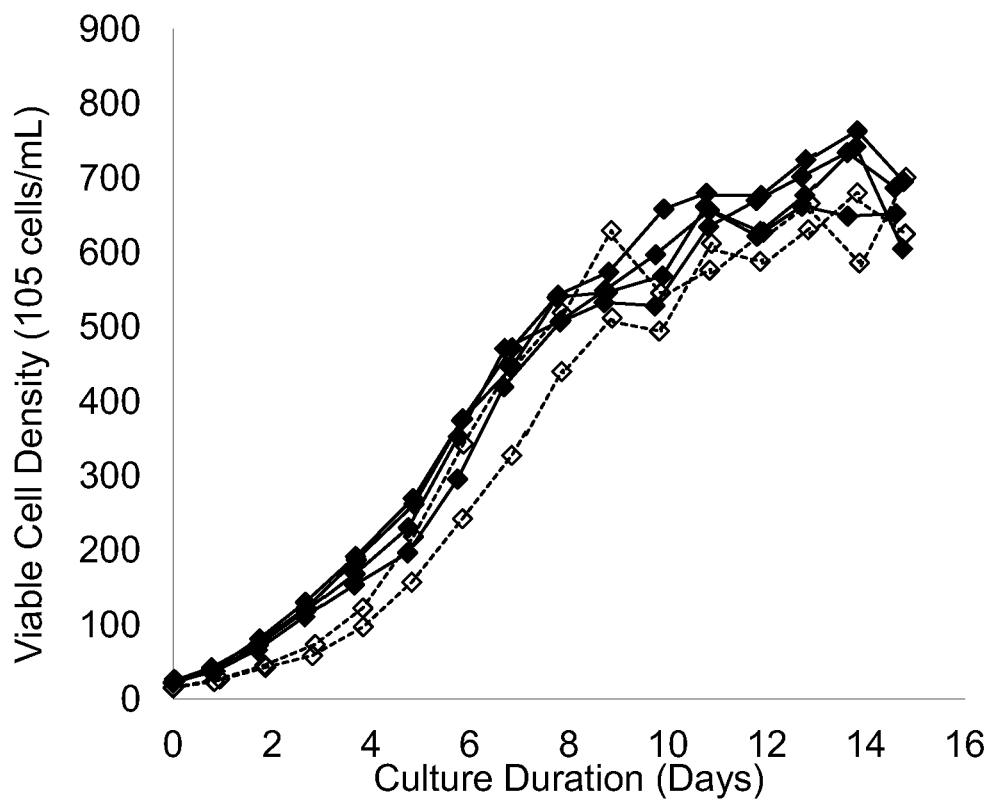
FIG. 6A Viable cell density.
Figure 6B:
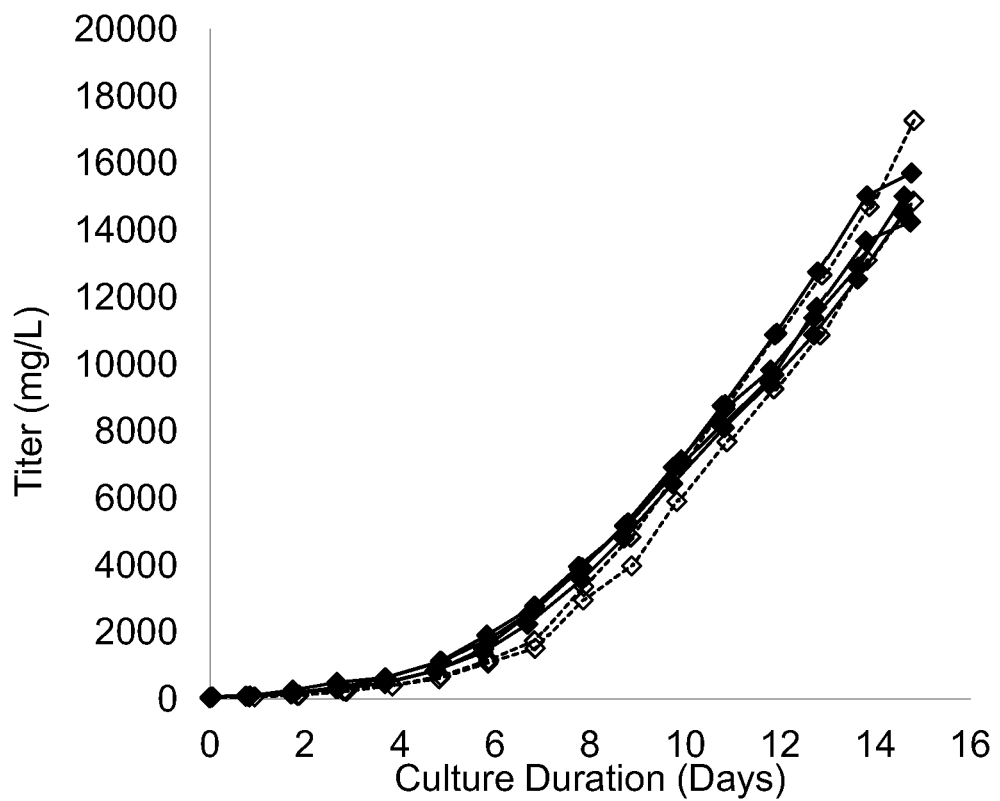
FIG. 6B Titer.
Figure 6C:
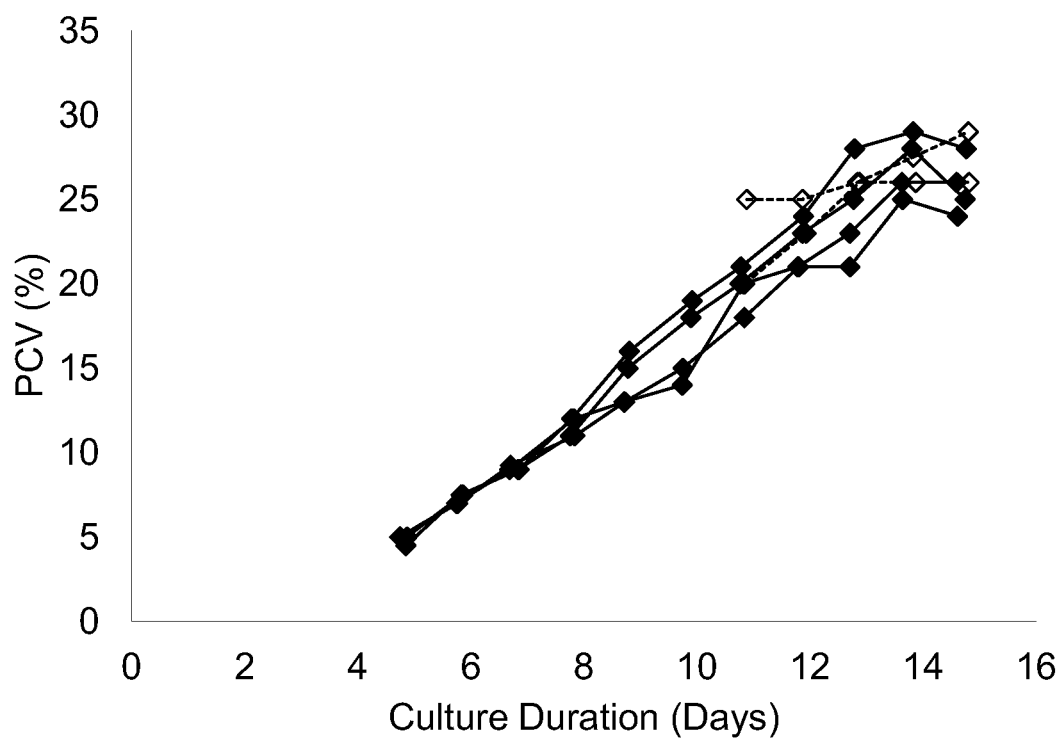
FIG. 6C Packed cell volume (PCV).
Figure 6D:
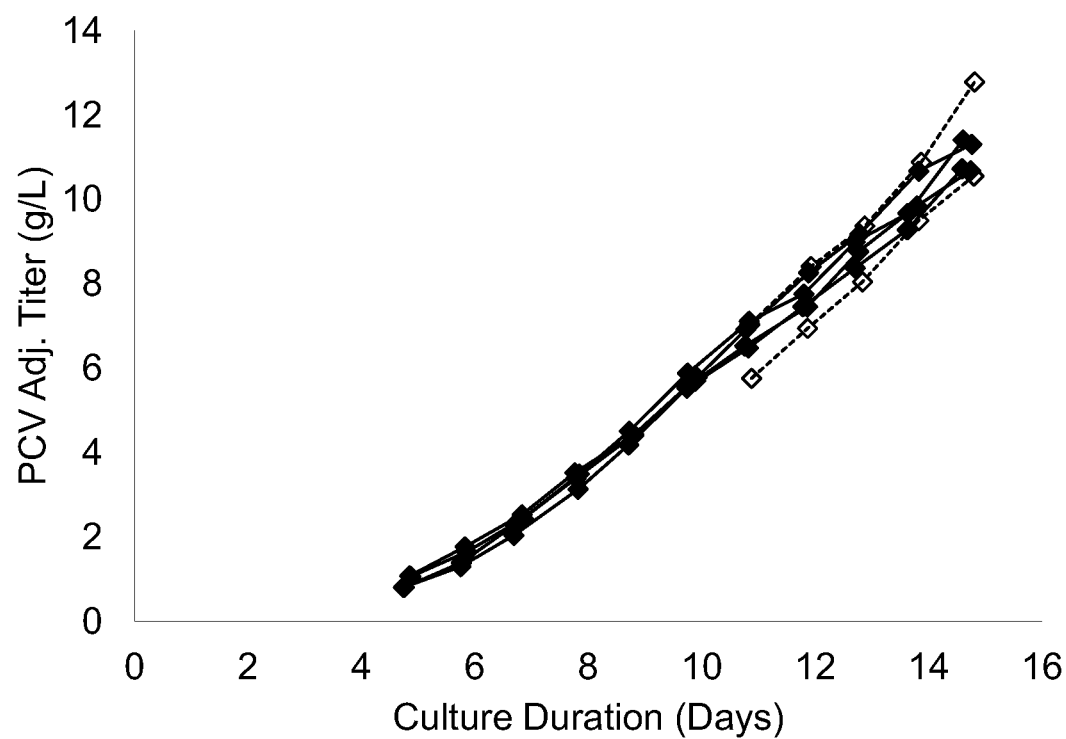
FIG. 6D PCV-adjusted titer.
Figure 6E:
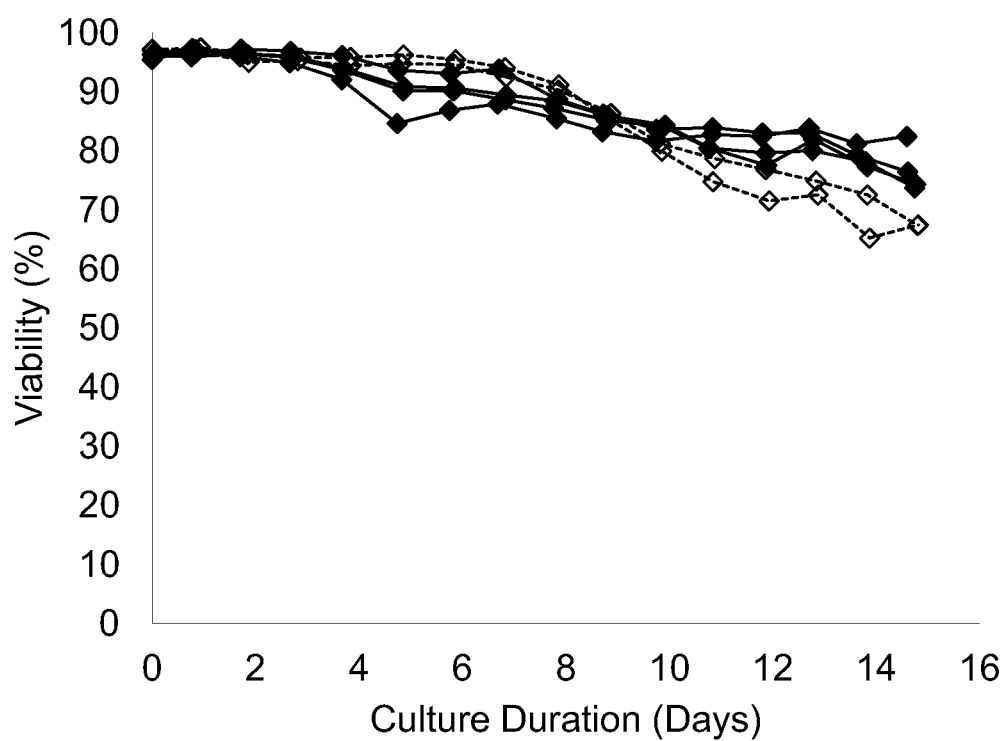
FIG. 6E Viability.

Data from four bench scale cultures and two pilot scale cultures is provided. VCD curves were similar at both scales, growth control was achieved (FIG. 6A), and the total cell mass (packed cell volume) was maintained below 30% at both scales (FIG. 6C). Although the VCD reached a plateau around day 10 or day 11, the packed cell volume continued to increase until about day 13 or 14 (FIG. 6C). Productivity was also similar between scales. Cultures perfused with media containing 5 mM asparagine made 14.2-15.7 g/L (10.7-11.4 g/L packed cell volume adjusted) at 2 L bench scale compared to 15.0-17.3 g/L (10.6-12.8 g/L packed cell volume adjusted) at 500 L pilot scale (FIGS. 6B and 6D). Viability trended slightly lower at the pilot scale (FIG. 6E).

What is claimed is:

1. A method of inducing growth arrest in a mammalian cell culture such that cells stop increasing in number, as measured by viable cell density (VCD), wherein the mammalian cells are Chinese Hamster Ovary (CHO) cells, comprising:
   establishing a mammalian cell culture in a serum-free culture medium in a bioreactor, wherein the mammalian cell culture is established by inoculating the bioreactor with at least $0.5 \times 10^6$ to $3.0 \times 10^6$ cells/mL;
   perfusing said culture with a serum-free perfusion medium having an L-asparagine concentration of 5 mM or less;
   maintaining the mammalian cells in by perfusion with a serum-free perfusion medium having an L-asparagine concentration of 5 mM or less, such that the cells stop increasing in number before viable cell density exceeds $1 \times 10^8$ cells/mL.

2. The method of claim 1, wherein the cell culture is transitioned from a growth phase to a production phase when viable cell density reaches at least $40 \times 10^6$ cells/mL.

3. The method according to claim 2, wherein perfusion with a serum-free perfusion medium having an L-asparagine concentration of 5 mM or less takes place prior to the production phase.

4. The method according to claim 2, wherein perfusion with a serum-free perfusion medium having an L-asparagine concentration of 5 mM or less takes place during the production phase.

5. The method according to claim 2, wherein the maximum VCD of said culture is further limited by a temperature shift from a first temperature to a second temperature, wherein the first temperature is between 35° C. and 38° C., and the second temperature is between 30° C. and 34° C.

6. The method according to claim 5, wherein the temperature shift occurs at the transition between the growth phase and production phase.

7. The method according to claim 5, wherein the temperature shift occurs during the production phase.

8. The method according to claim 2, wherein the perfusion with a serum-free perfusion medium having an L-asparagine concentration of 5 mM or less begins prior to or during production phase.

9. The method according to claim 2, wherein the packed cell volume, as measured by the ratio of the volume occupied by the cells to the total volume of cell culture, during the production phase is less than or equal to 35%.

10. The method according to claim 2, wherein the packed cell volume during the production phase is less than or equal to 30%.

11. The method according to claim 2, wherein the viable cell density of the mammalian cell culture during the production phase is from $25\times10^6$ viable cells/ml to $80\times10^6$ viable cells/ml.

12. The method according to claim 2, wherein perfusion is performed at a rate that increases during the production phase from 0.25 working volume per day to 1.0 working volume per day during the cell culture.

13. The method according to claim 1, wherein said CHO cell lacks asparagine synthetase.

14. The method according to claim 1, further comprising a temperature shift from 36° C. to 31° C.

15. The method according to claim 14, wherein the temperature shift occurs at the transition between a growth phase and a production phase.

16. The method according to claim 14, wherein the temperature shift occurs during a production phase.

17. The method according to claim 1, further comprising a temperature shift from 36° C. to 33° C.

18. The method according to claim 1, wherein the maximum VCD of said culture is reduced as compared to a control, and wherein said control is the maximum VCD of the culture maintained by perfusion with a serum-free perfusion medium having an L-asparagine concentration higher than 5 mM.

19. The method according to claim 1, wherein the maximum VCD of said culture is further limited by a temperature shift from a first temperature to a second temperature, wherein the first temperature is between 35° C. and 38° C., and the second temperature is between 30° C. and 34° C.

20. The method according to claim 1, wherein the perfusion with a serum-free perfusion medium having an L-asparagine concentration of 5 mM or less begins when viable cell density reaches $40\times10^6$ cells/mL or more.

21. The method according to claim 1, wherein the perfusion with a serum-free perfusion medium having an L-asparagine concentration of 5 mM or less begins when viable cell density reaches $50\times10^6$ cells/mL or more.

22. The method according to claim 1, wherein the perfusion with a serum-free perfusion medium having an L-asparagine concentration of 5 mM or less begins when viable cell density reaches $60\times10^6$ cells/mL or more.

23. The method according to claim 1, wherein the perfusion with a serum-free perfusion medium having an L-asparagine concentration of 5 mM or less begins when viable cell density reaches $80\times10^6$ cells/mL or more.

24. The method according to claim 1, wherein the concentration of L-asparagine in the serum-free perfusion medium is less than or equal to 4.0 mM.

25. The method according to claim 1, wherein the concentration of L-asparagine in the serum-free perfusion medium is less than or equal to 3.0 mM.

26. The method according claim 1, wherein the concentration of L-asparagine in the serum-free perfusion medium is less than or equal to 2.0 mM.

27. The method according to claim 1, wherein the concentration of L-asparagine in the serum-free perfusion medium is less than or equal to 1.0 mM.

28. The method according to claim 1, wherein the concentration of L-asparagine in the serum-free perfusion medium is 0 mM.

29. The method according to claim 1, wherein the L-asparagine concentration of the cell culture medium is monitored.

30. The method according to claim 1, wherein perfusion comprises continuous perfusion.

31. The method according to claim 1, wherein the rate of perfusion is constant.

32. The method according to claim 1, wherein perfusion is performed at a rate of less than or equal to 1.0 working volumes per day.

33. The method according to claim 1, wherein the perfusion is accomplished by alternating tangential flow.

34. The method according claim 1, wherein the bioreactor has a capacity of at least 500 L.

35. The method according to claim 1, wherein the bioreactor has a capacity of 500 L to 2000 L.

36. The method according to claim 1, wherein the bioreactor has a capacity of 1000 L to 2000 L.

37. The method of claim 1, wherein said cells are cultured in a serum-free medium having an L-asparagine concentration higher than 5 mM before perfusing with a serum-free perfusion medium having an L-asparagine concentration of 5 mM or less.

38. The method of claim 1, wherein said cells are cultured in a serum-free medium having an L-asparagine concentration higher than 5 mM until VCD is at least $20\times10^6$ cells/mL, before perfusing with a serum-free perfusion medium having an L-asparagine concentration of 5 mM or less.

39. A method of inducing growth arrest of a mammalian cell culture in a bioreactor, such that cells stop increasing in number, as measured by viable cell density (VCD), wherein the mammalian cells are Chinese Hamster Ovary (CHO) cells, comprising:
   establishing a CHO cell culture in a serum-free culture medium in a bioreactor, wherein the mammalian cell culture is established by inoculating the bioreactor with at least $0.5\times10^6$ to $3.0\times10^6$ cells/mL;
   perfusing said culture with a serum-free perfusion medium having an L-asparagine concentration of 5 mM or less;
   maintaining the mammalian cells in by perfusion with a serum-free perfusion medium having an L-asparagine concentration of 5 mM or less, such that the packed cell volume does not exceed 35%.

40. The method of claim 39, wherein said cells are cultured in a serum-free medium having an L-asparagine concentration higher than 5 mM before perfusing with a serum-free perfusion medium having an L-asparagine concentration of 5 mM or less.

41. The method of claim 39, wherein said cells are cultured in a serum-free medium having an L-asparagine concentration higher than 5 mM until VCD is at least $20\times10^6$ cells/mL, before perfusing with a serum-free perfusion medium having an L-asparagine concentration of 5 mM or less.

* * * * *